US012727746B2

(12) United States Patent
Reed et al.

(10) Patent No.: US 12,727,746 B2
(45) Date of Patent: Sep. 8, 2026

(54) ASEPTIC FILLING TECHNIQUES AND SYSTEMS FOR AN ENDOSCOPE

(71) Applicant: Boston Scientific Scimed, Inc., Maple Grove, MN (US)

(72) Inventors: Brittany Elizabeth Reed, Brighton, MA (US); Brian Luis, Boylston, MA (US); Ryan V. Wales, Northborough, MA (US); Aakash Deora, Marlborough, MA (US); Juan M. Alvarez Azpeitia, Somerville, MA (US); Nathan Thomas Cummings, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 357 days.

(21) Appl. No.: 18/450,893

(22) Filed: Aug. 16, 2023

(65) Prior Publication Data

US 2024/0057855 A1 Feb. 22, 2024

Related U.S. Application Data

(60) Provisional application No. 63/399,543, filed on Aug. 19, 2022.

(51) Int. Cl.
*A61B 1/015* (2006.01)
*A61B 1/00* (2006.01)
*A61B 1/12* (2006.01)

(52) U.S. Cl.
CPC .............. *A61B 1/015* (2013.01); *A61B 1/126* (2013.01); *A61B 1/00131* (2013.01)

(58) Field of Classification Search
USPC .................................................. 600/158, 159
See application file for complete search history.

(56) References Cited

U.S. PATENT DOCUMENTS 3,750,692 A * 8/1973 Tibbs ...................... A61M 1/61 141/59
4,136,696 A * 1/1979 Nehring ............. A61M 3/0262 604/142
4,289,158 A * 9/1981 Nehring .................. A61M 1/61 137/205
5,133,336 A 7/1992 Savitt et al.
5,297,537 A 3/1994 Savitt et al.
(Continued)

FOREIGN PATENT DOCUMENTS

EP 0123817 A1 11/1984
EP 2090217 A1 8/2009
(Continued)

OTHER PUBLICATIONS

International Search Report and Written Opinion dated Nov. 21, 2023 for International Application No. PCT/US2023/072320.

*Primary Examiner* — John P Leubecker
(74) *Attorney, Agent, or Firm* — Seager, Tufte & Wickhem, LLP

(57) ABSTRACT

Methods and systems for refilling a container during an endoscopic procedure. An illustrative reservoir may be placed in selective fluid communication with a water bottle. The water bottle may form a fluid tight seal with the reservoir to transfer water from the water bottle to the reservoir. A water storage chamber may be coupled to a first container and/or a second container.

8 Claims, 14 Drawing Sheets

(56) References Cited

U.S. PATENT DOCUMENTS

| | | | | |
|---|---|---|---|---|
| 5,328,478 | A | 7/1994 | McVay | |
| 5,503,553 | A * | 4/1996 | Hines | A46B 11/063 601/162 |
| 5,536,254 | A | 7/1996 | McVay | |
| 8,696,552 | B2 | 4/2014 | Whitman | |
| 9,332,894 | B2 | 5/2016 | Cheng et al. | |
| 10,098,525 | B2 | 10/2018 | Maurice | |
| 10,357,148 | B2 | 7/2019 | Ramsey | |
| 11,576,566 | B2 | 2/2023 | Pollock et al. | |
| 2001/0033805 | A1 | 10/2001 | Jacobs et al. | |
| 2002/0064880 | A1* | 5/2002 | Merten | B01F 35/8822 422/63 |
| 2005/0130473 | A1* | 6/2005 | Annecke | A61B 1/125 439/135 |
| 2006/0276689 | A1 | 12/2006 | Litscher et al. | |
| 2007/0135779 | A1* | 6/2007 | Lalomia | F24F 8/158 604/319 |
| 2009/0221977 | A1* | 9/2009 | Blott | A61M 3/02 604/290 |
| 2010/0152653 | A1* | 6/2010 | Hoke | A61M 3/0201 604/94.01 |
| 2012/0302836 | A1 | 11/2012 | Boulais et al. | |
| 2019/0001029 | A1* | 1/2019 | Davie | A61M 1/60 |
| 2020/0114138 | A1* | 4/2020 | Haury | A61M 5/16827 |
| 2022/0192478 | A1 | 6/2022 | Pollock et al. | |
| 2022/0192479 | A1 | 6/2022 | Harris et al. | |

FOREIGN PATENT DOCUMENTS

| | | | |
|---|---|---|---|
| JP | H11-128325 | A | 5/1999 |
| JP | 2001321332 | A | 11/2001 |
| JP | 2009-536552 | A | 10/2009 |
| WO | 2022140443 | A1 | 6/2022 |

* cited by examiner 500
502
504
506
508
510
512
514
516
518
520
522
524
526
528
530
532
534
536
538
540
542
546
548
550
552
554
556
558
560
562
564
566
568
570
572
574

ASEPTIC FILLING TECHNIQUES AND SYSTEMS FOR AN ENDOSCOPE

CROSS-REFERENCE TO RELATED APPLICATIONS

This application claims the benefit of U.S. Provisional Patent Application Ser. No. 63/399,543 filed on Aug. 19, 2022, the disclosure of which is incorporated herein by reference.

FIELD

This disclosure relates generally to medical fluid containers and methods, and particularly to methods and/or systems for refilling or providing refillable container to supply fluid and/or gas to an endoscope.

BACKGROUND

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. To enable these capabilities compressed gasses from either the processor or alternative source are used to insufflate the working lumen or increase the pressure within a fluid bottle which washes the lens of the endoscope. Additionally, a peristaltic pump can be used to irrigate the working lumen of debris. One of the challenges faced during endoscopic procedures is that the common water bottle and tube set used contain a maximum of 1 liter of water and are not designed to be refilled. This may force nurses/technicians to replace the water bottle multiple times a day. This may introduce multiple opportunities for contamination to the tube set by either contacting non-sterile surfaces or dropping the tubing on the floor.

It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first example, a fitting arranged and configured to couple to one or more water bottles to refill a fluid reservoir for use in an endoscopic procedure may comprise a first coupling portion in fluid communication with a first fluid path, a second coupling portion in fluid communication with a second fluid path, a fluid outlet, and an actuatable valve in fluid communication with the first fluid path, the second fluid path and the fluid outlet. The actuatable valve may be configured to selectively fluidly couple the first fluid path, the second fluid path and the fluid outlet.

Alternatively or additionally to any of the examples above, in another example, the fluid outlet may be disposed in a plane generally orthogonal to a plane of the first and second fluid paths.

Alternatively or additionally to any of the examples above, in another example, the fluid outlet may be disposed between the first coupling portion and the second coupling portion.

Alternatively or additionally to any of the examples above, in another example, the actuatable valve may comprise a rotatable valve.

Alternatively or additionally to any of the examples above, in another example, the first coupling portion may comprise a threaded coupling.

Alternatively or additionally to any of the examples above, in another example, the first coupling portion may be configured to engage external threads of a water bottle.

Alternatively or additionally to any of the examples above, in another example, the second coupling portion may comprise a threaded coupling.

Alternatively or additionally to any of the examples above, in another example, the second coupling portion may be configured to engage external threads of a water bottle.

Alternatively or additionally to any of the examples above, in another example, the first coupling portion may comprise a blunt needle tip.

Alternatively or additionally to any of the examples above, in another example, the blunt needle tip may be configured to puncture a pierceable cap of a water bottle.

Alternatively or additionally to any of the examples above, in another example, the second coupling portion may comprise a blunt needle tip.

Alternatively or additionally to any of the examples above, in another example, the blunt needle tip may be configured to puncture a pierceable cap of a water bottle.

In another example, a reservoir arranged and configured to couple to an endoscope for use in an endoscopic procedure may comprise a container configured to contain a fluid therein, the container having a top and a bottom, a water outlet, a gas inlet, and a tubular port extending outward from the container at or near the top of the container. The tubular port may be configured to puncture a water bottle cap and form a fluid-tight seal between the tubular port and the water bottle cap.

Alternatively or additionally to any of the examples above, in another example, the reservoir may further comprise a removable cap releasably secured to the tubular port.

Alternatively or additionally to any of the examples above, in another example, an outer diameter of the tubular port may be approximately the same as an inner diameter of a neck of a water bottle.

Alternatively or additionally to any of the examples above, in another example, the reservoir may be free-standing.

Alternatively or additionally to any of the examples above, in another example, the reservoir may further comprise a water bottle fluidly coupled to the tubular port.

Alternatively or additionally to any of the examples above, in another example, the water bottle may have a volume in a range of about 0.5 liters to about 20 liters.

In another example, a method for filling a reservoir arranged and configured to couple to an endoscope for use in an endoscopic procedure may comprise uncoupling a second end of a water supply tubing from a connector in fluid communication with an endoscope, the water supply tubing extending from the second end to a first end in fluid communication with a reservoir of an endoscope system, positioning the second end of the water supply tubing in fluid communication with a water bottle, and activating a pump that is coupled to the water supply tubing to pump water from the water bottle through the water supply tubing to the reservoir.

Alternatively or additionally to any of the examples above, in another example, the method may further comprise reversing a direction of flow of the pump prior to activating the pump.

Alternatively or additionally to any of the examples above, in another example, the water supply tubing may comprise a lens wash tubing.

Alternatively or additionally to any of the examples above, in another example, the water supply tubing may comprise an irrigation supply tubing.

Alternatively or additionally to any of the examples above, in another example, the method may further comprise by-passing a one-way valve in line with the irrigation supply tubing prior to activating the pump.

In another example, a reservoir arranged and configured to couple to an endoscope for use in an endoscopic procedure may comprise a container configured to contain a fluid therein, the container having a top and a bottom, a water outlet, a gas inlet, and one or more threaded openings formed in the top of the container. The one or more threaded openings may be configured to threadably engage a water bottle.

Alternatively or additionally to any of the examples above, in another example, the reservoir may further comprise one or more removable caps. The one or more removable caps may be configured to selectively seal the one or more threaded openings.

Alternatively or additionally to any of the examples above, in another example, the one or more threaded openings may comprise at least two threaded openings.

Alternatively or additionally to any of the examples above, in another example, a volume of the container may be less than a volume of a water bottle configured to couple to the one or more threaded openings.

In another examples, a reservoir arranged and configured to couple to an endoscope for use in an endoscopic procedure may comprise a first container configured to contain a fluid therein, the first container having a first water outlet and a gas inlet, a second container configured to contain a fluid therein, the second container having a second water outlet, and a chamber in fluid communication with the first container and the second container. The chamber may comprise one or more ports configured to selectively fluidly couple the chamber with an external water source.

Alternatively or additionally to any of the examples above, in another example, the first container may be threadably engaged with the chamber.

Alternatively or additionally to any of the examples above, in another example, the second container may be threadably engaged with the chamber.

Alternatively or additionally to any of the examples above, in another example, the reservoir may further comprise a water supply tube including a first end, a second end, and a first lumen extending therethrough, wherein the first lumen is in fluid communication with the first container and the second end of the water supply tube is positioned external to the chamber and the first container and a gas supply tube including a first end, a second end, and a second lumen extending therethrough, wherein the second lumen is in operative fluid communication with the first container and the second end of the gas supply tube is positioned external to the chamber and the first container.

Alternatively or additionally to any of the examples above, in another example, the first lumen may extend through the chamber.

Alternatively or additionally to any of the examples above, in another example, the second lumen may extend through the chamber.

Alternatively or additionally to any of the examples above, in another example, the reservoir may further comprise an irrigation supply tube including a first end, a second end, and an irrigation lumen extending therethrough, wherein the irrigation lumen is in fluid communication with the second container and the second end of the irrigation supply tube is positioned external to the chamber and the second container.

Alternatively or additionally to any of the examples above, in another example, the irrigation lumen may extend through the chamber.

Alternatively or additionally to any of the examples above, in another example, the reservoir may further comprise one or more supports coupled to the chamber. The one or more supports may be configured to engage one or more hooks.

Alternatively or additionally to any of the examples above, in another example, the reservoir may further comprise a partition positioned within the chamber partitioning the chamber into a first sub-chamber and a second sub-chamber.

Alternatively or additionally to any of the examples above, in another example, the partition may be configured to fluidly isolate the first sub-chamber and the second sub-chamber.

Alternatively or additionally to any of the examples above, in another example, the one or more ports may be configured to selectively fluidly couple the first sub-chamber or the second sub-chamber with the external water source.

Alternatively or additionally to any of the examples above, in another example, the one or more ports may comprise a first port in fluid communication with the first sub-chamber and a second port in fluid communication with the second sub-chamber.

Alternatively or additionally to any of the examples above, in another example, the first sub-chamber may be in fluid communication with the first container and the second sub-chamber may be in fluid communication with the second container.

Alternatively or additionally to any of the examples above, in another example, the reservoir may further comprise one or more removable seals removably coupled to the one or more ports.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
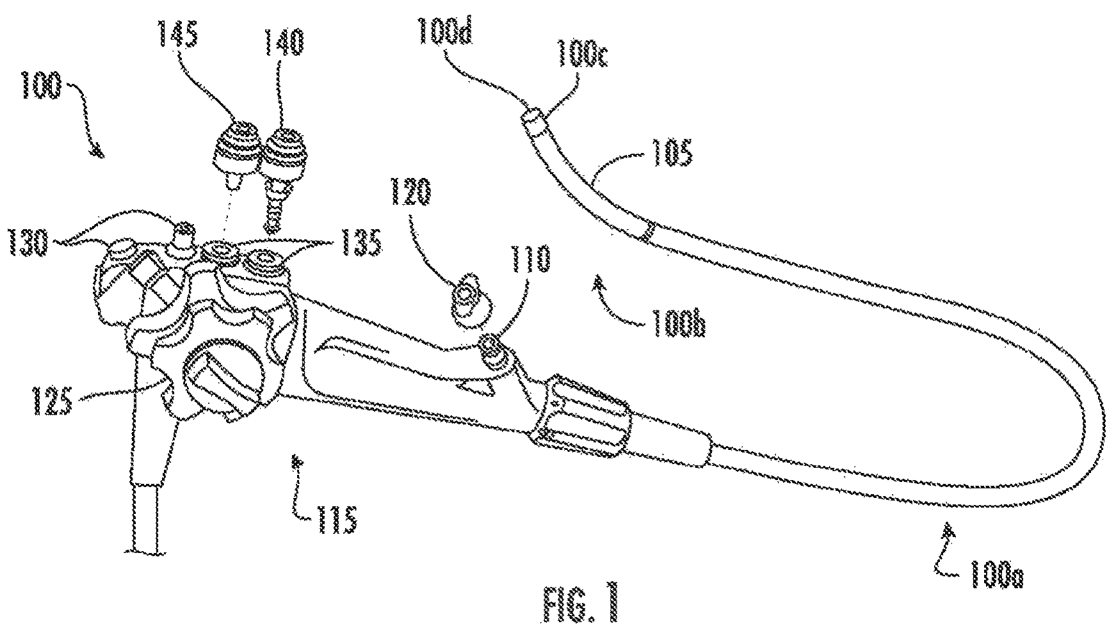
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, the same or similar reference numbers will be used through the drawings to refer to the same or like parts.

The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Embodiments of the present disclosure are described with specific reference to a bottle (e.g., container, reservoir, or the like) and tube assembly or set. It should be appreciated that such embodiments may be used to supply fluid and/or gas to an endoscope, for a variety of different purposes, including, for example to facilitate insufflation of a patient, lens washing, and/or to irrigate a working channel to aid in flushing/suctioning debris during an endoscopic procedure.

Although the present disclosure includes descriptions of a container and tube set suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. To enable these capabilities compressed gasses from either the processor or alternative source are used to increase the pressure within a fluid bottle which either insufflates the working lumen or wash the lens of the endoscope. Additionally, a peristaltic pump can be used to irrigate the working lumen of debris. One of the challenges faced during endoscopic procedures is that the common water bottle and tube set used contain a maximum of 1 liter of water and are not designed to be refilled. This may force nurses/technicians to replace the water bottle multiple times a day. This may introduce multiple opportunities for contamination to the tube set by either contacting non-sterile surfaces or dropping the tubing on the floor. Disclosed herein are methods and systems to reduce or eliminate the need to disconnect the tube set and use a second bottle.

Figure 2:
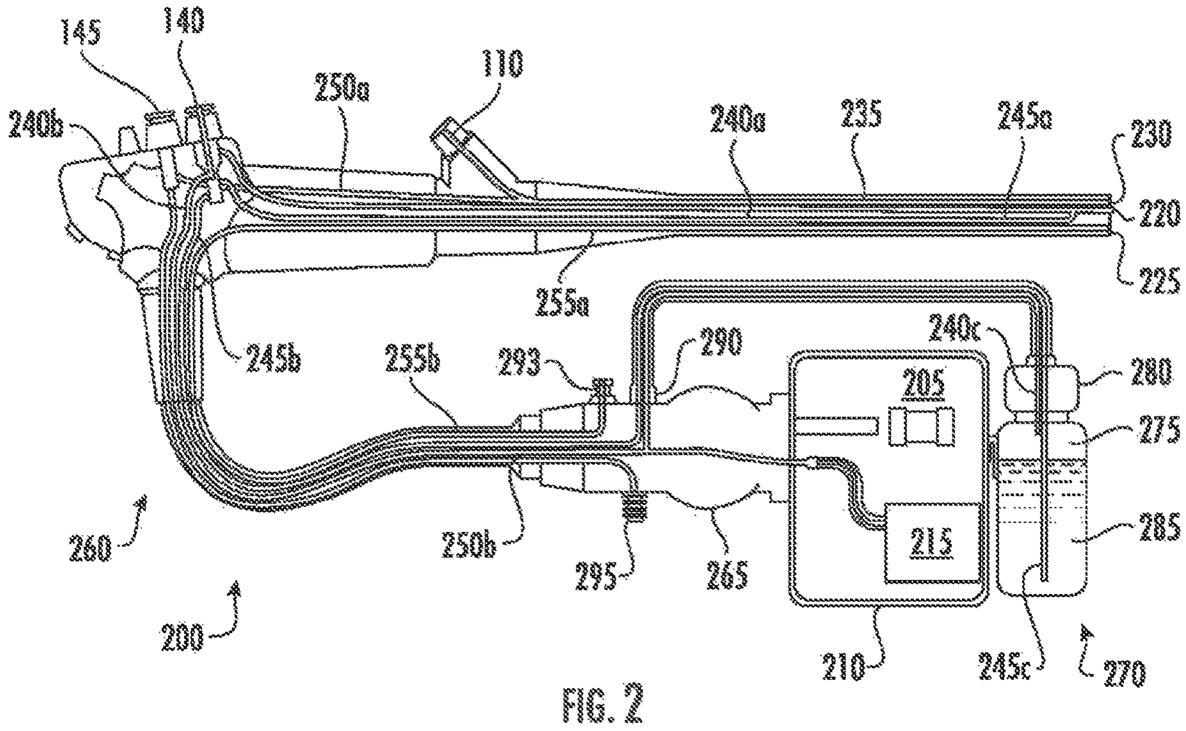
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 are depicted that may comprise an elongated shaft 100*a* that is inserted into a patient. A light source 205 feeds illumination light to a distal portion 100*b* of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100*a* may include a distal tip 100*c* provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the patient at the treatment area and for supplying water to wash a lens covering the imager. An irrigation opening 225 in the end face 100*d* supplies irrigation fluid to the treatment area of the patient. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 extends along the shaft 100*a* to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240*a* and a lens wash supply line 245*a* run distally from the gas/water valve 140 along the shaft 100*a* and converge at the distal tip 100*c* proximal to the gas/wash nozzle 220 (FIG. 2). The other valve well 135 receives a suction valve 145 for operating a suction operation. A suction supply line 250*a* runs distally from the suction valve 145 along the shaft 100*a* to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$) feed line 240*b*, a lens wash feed line 245*b*, a suction feed line 250*b*, an irrigation feed line 255*b*, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100*a* to transmit light to the distal tip 100*c* of the endoscope 100. The connector portion 265 when plugged into the video processing unit 210 also connects the air pump 215 to the gas feed line 240*b* in the umbilical 260.

A water reservoir or container 270 (e.g., water bottle) is fluidly connected to the endoscope 100 through the connector portion 265 and the umbilical 260. A length of gas supply tubing 240*c* passes from one end positioned in an air gap 275 between the top 280 (e.g., bottle cap) of the reservoir 270 and the remaining water 285 in the reservoir to a detachable gas/lens wash connection 290 on the outside of the connector portion 265. The detachable gas/lens wash connection 290 may be detachable from the connector portion 265 and/or the gas supply tubing 240*c*. The gas feed line 240*b* from the umbilical 260 branches in the connector portion 265 to fluidly communicate with the gas supply tubing 240*c* at the detachable gas/lens wash connection 290, as well as the air pump 215. A length of lens wash tubing 245*c*, with one end positioned at the bottom of the reservoir 270, passes through the top 280 of the reservoir 270 to the same detachable connection 290 as the gas supply tubing 240*c* on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255*b* in the umbilical 260. The detachable irrigation connection 293 may be detachable from the connector portion 265 and/or the irrigation supply tubing (not shown). In some embodiments, irrigation water is supplied via a pump (e.g., peristaltic pump) from a water source independent (not shown) from the water reservoir 270. In other embodiments, the irrigation supply tubing and lens wash tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100. The detachable suction connection 295 may be detachable from the connector portion 265 and/or the suction feed line 250*b* and/or the vacuum source.

The gas feed line 240*b* and lens wash feed line 245*b* are fluidly connected to the valve well 135 for the gas/water valve 140 and configured such that operation of the gas/water valve in the well controls supply of gas or lens wash to the distal tip 100*c* of the endoscope 100. The suction feed line 250*b* is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connector portion 265 and branched to the gas/water valve 140 on the operating handle 115 through the gas feed line 240*b* in the umbilical 260, as well as through the gas supply tubing 240*c* to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240*a* and out the distal tip 100*c* of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245*c*, through the connector portion 265, umbilical 260, through the gas/water valve 140 and down the lens wash supply line 245*a*, converging with the gas supply line 240*a* prior to exiting the distal tip 100*c* of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245*c*, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240*c* to filter-out undesired contaminants or particulates from passing into the water reservoir 270. In some embodiments, outflow check valves or other one-way valve configurations (not shown) may be placed in the path of the lens wash supply tubing to help prevent water from backflowing into the reservoir 270 after the water has passed the valve.

A relatively higher flow rate of irrigation water is typically required compared to lens wash, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump is connected to the irrigation feed line 255*b* in the umbilical 260 and the irrigation supply line 255*a* endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255*b* in the umbilical, and down the irrigation supply line in the shaft 100*a* of the endoscope to the distal tip 100*c*. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash tubing 245*c*, may be placed in the path of the irrigation supply tubing to help prevent back-flow into the reservoir after water has passed the valve.

FIGS. 3A-3D are schematic drawings illustrating the operation of an embodiment of a hybrid system 300 where the supply tubing for irrigation and lens wash are connected to and drawn from a single water reservoir. It is contemplated that fluids other than water may be used, such as, but not limited to saline. The hybrid system 300 includes the single water reservoir 305, a cap 310 for the reservoir, gas supply tubing 240*c*, lens wash supply tubing 245*c*, irrigation pump 315 with foot switch 318, upstream irrigation tubing 320 and downstream irrigation supply tubing 255*c*. The cap 310 may be configured to attach in a seal-tight manner to the water reservoir 305 by a typically threaded arrangement. The cap 310 may include a gasket to seal the cap 310 to the reservoir 305. The gasket can be an O-ring, flange, collar, and/or the like and can be formed of any suitable material. A number of through-openings (325*a*, 325*b*, 325*c*) in the cap 310 are provided to receive, respectively, the gas supply tubing 240*c*, lens wash supply tubing 245*c*, and upstream irrigation supply tubing 320. In FIGS. 3A-3D, the system depicted includes separate tubing for gas supply, lens wash, and irrigation.

In other embodiments, the gas supply tubing 240*c* and lens wash tubing 245*c* may be combined in a coaxial arrangement. Some illustrative coaxial arrangements are described in commonly assigned U.S. patent application Ser. No. 17/558,239, titled INTEGRATED CONTAINER AND TUBE SET FOR FLUID DELIVERY WITH AN ENDOSCOPE and U.S. patent application Ser. No. 17/558,256, titled TUBING ASSEMBLIES AND METHODS FOR FLUID DELIVERY, the disclosures of which are hereby incorporated by reference. For example, the gas supply tubing may define a lumen that is sufficiently large in diameter to encompass a smaller diameter lens wash tubing, coaxially received within the gas supply tubing, as well as provide air to the water source in an annular space surrounding the lens wash tubing to pressurize the water reservoir (see, e.g., gas and lens wash supply tubing 240*c*, 245*c*). The lens wash supply tubing may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion (e.g., connector portion 265 of FIG. 2).

In various embodiments, different configurations of valving (not shown) may be incorporated into various embodiments disclosed hereby, including the tubing of the system 200, 300. For example, an in-flow check valve can be disposed in the path of the gas supply tubing 240*c* to help prevent backflow into the air pump 215. In this manner, pressure building within the water reservoir 305 creates a pressure difference between the water source and the gas supply tubing 240*c* helping to maintain a positive pressure in the water source even when large amounts of water may be removed from the water source during the irrigation function. This arrangement compensates for any time lag in air being delivered from the air pump 215 to the water reservoir 305, which might otherwise cause a negative pressure vacuum in the water reservoir. Similarly, an outflow check valve, such as the one-way valve with inlet/outlets and valve insert, may be incorporated in the lens wash supply tubing 240*c*, upstream irrigation supply tubing 320, and/or downstream irrigation supply tubing 255*c* to help prevent backflow of water from either or both of the lens wash and irrigation tubing in the event of a negative pressure situation, as described.

More generally, in many embodiments, a check valve may refer to any type of configuration for fluid to flow only in one direction in a passive manner. For example, a check valve may include, or refer to, one or more of a ball check valve, a diaphragm check valve, a swing check valve, a tilting disc check valve, a flapper valve, a stop-check valve, a lift-check valve, an in-line check valve, a duckbill valve, a pneumatic non-return valve, a reed valve, a flow check. Accordingly, a check valve as used herein is meant to be separate and distinct from an active valve that is operated in a binary manner as an on/off valve or switch to allowed flow to be turned on or allow flow to be turned off (e.g., a stop cock valve, solenoid valve, peristaltic pump).

During operation of the system of FIGS. 3A-3D, a flow of water for irrigation may be achieved by operating the irrigation pump 315. A flow of water for lens wash may be achieved by depressing the gas/water valve 140 on the operating handle 115 of the endoscope 100. These functions may be performed independent of one another or simultaneously. When operating lens wash and irrigation at the same time, as fluid is removed from the water reservoir 305, the pressure in the system may be controlled to maintain the lens wash supply tubing 240*c* at substantially the pressure necessary to accomplish a lower flow rate lens wash, while compensating for reduced pressure in the water reservoir 305 due to supplying a high flow rate irrigation. When pressure is reduced in the water reservoir by use of the lens wash function, the irrigation function, or both functions simultaneously, the reduced pressure may be compensated for by the air pump 215 via the gas supply tubing 240*c*.

Figures 3A, 3B:
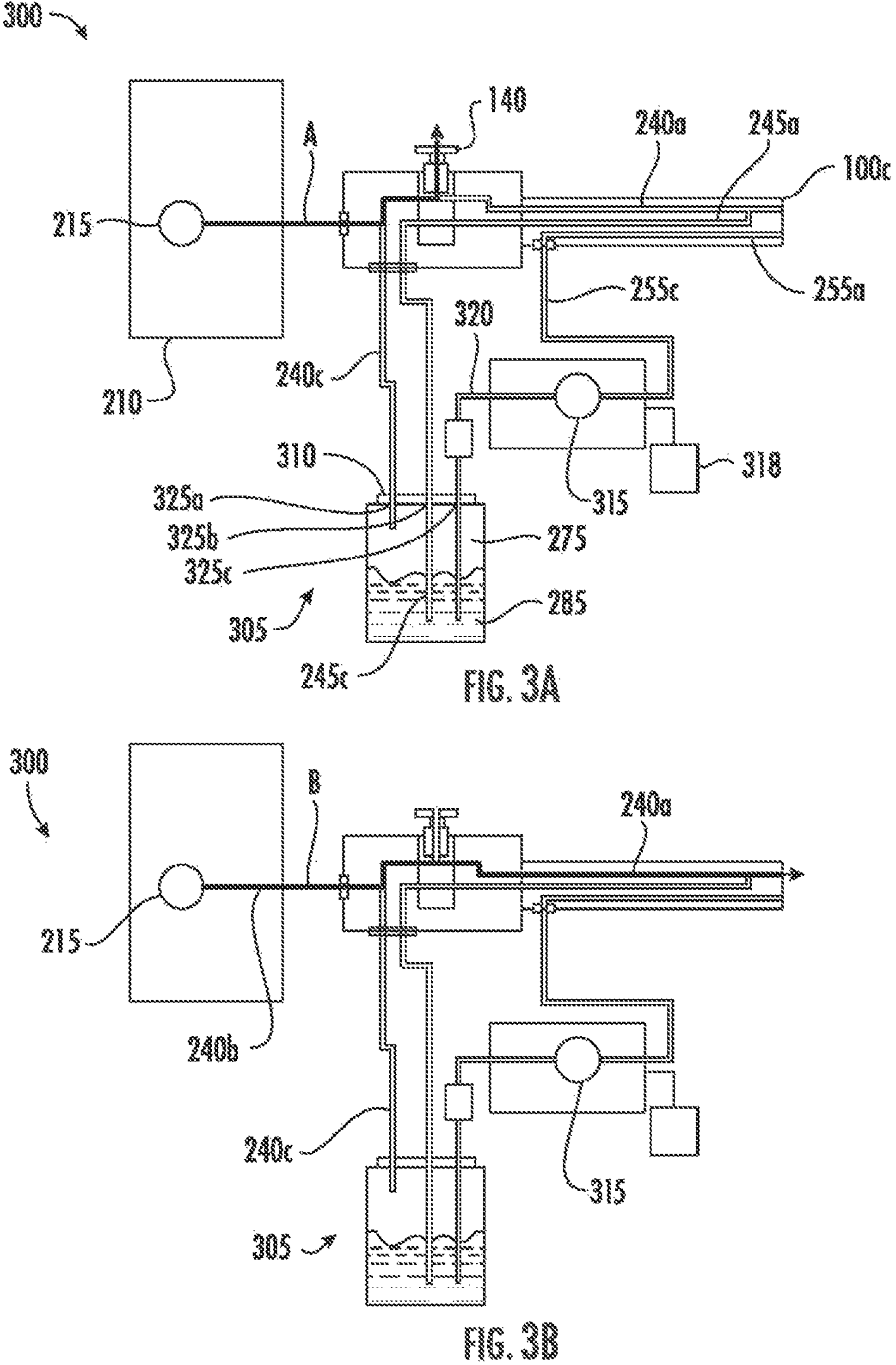
FIG. 3A depicts an endoscope system with endoscope, light source, water reservoir, and tubing assembly for hybrid air, lens wash and irrigation fluid delivery, wherein the system is activated to deliver air to atmosphere.
FIG. 3B depicts the endoscope system of FIG. 3A, wherein the system is activated to deliver air to a patient through the patient end of the endoscope.

The schematic set-up in FIGS. 3A-3D has been highlighted to show the different flow paths possible with the hybrid system 300 having supply tubing for irrigation 320 and lens wash 240*c* connected to and drawn from the single water reservoir 305. As shown in FIG. 3A, the endoscope 100 is in a neutral state with the gas/water valve 140 in an open position. The neutral state delivers neither gas, nor lens wash, to the distal tip of the endoscope. Rather gas (pressure) is delivered along path A from the pressurizing air pump 215 and vented through the gas feed line 240*b* in the umbilical 260 via the connector portion 265 and through the gas/water valve to atmosphere. Since the system is open at the vent hole in the gas/water valve 140, there is no build up to pressurize the water reservoir 305 and consequently no water is pushed through the lens wash supply tubing 240*c*.

As shown in FIG. 3B, the endoscope 100 is in a gas delivery state with the gas/water valve 140 in a first position. When gas is called for at the distal tip 100*c*, for example, to clean the end face 100*d* of the distal tip or insufflate the patient body in the treatment area, the user closes off the vent hole in the gas/water valve 140 with a thumb, finger, or the like (first position). In this state, gas (pressure) is delivered along path B from the air pump 215 and flowed through the gas feed line 240*b* in the umbilical 260 via the connector portion 265. The gas continues through the gas/water valve 140 to the gas supply line 240*a* in the endoscope shaft 100*a* and out the gas/lens wash nozzle 220 at the distal tip 100*c*. There is no build up to pressurize the water reservoir since the system is open at the gas/lens water nozzle 220, and consequently no water is pushed through the lens wash supply tubing 240*c*.

Figures 3C, 3D:
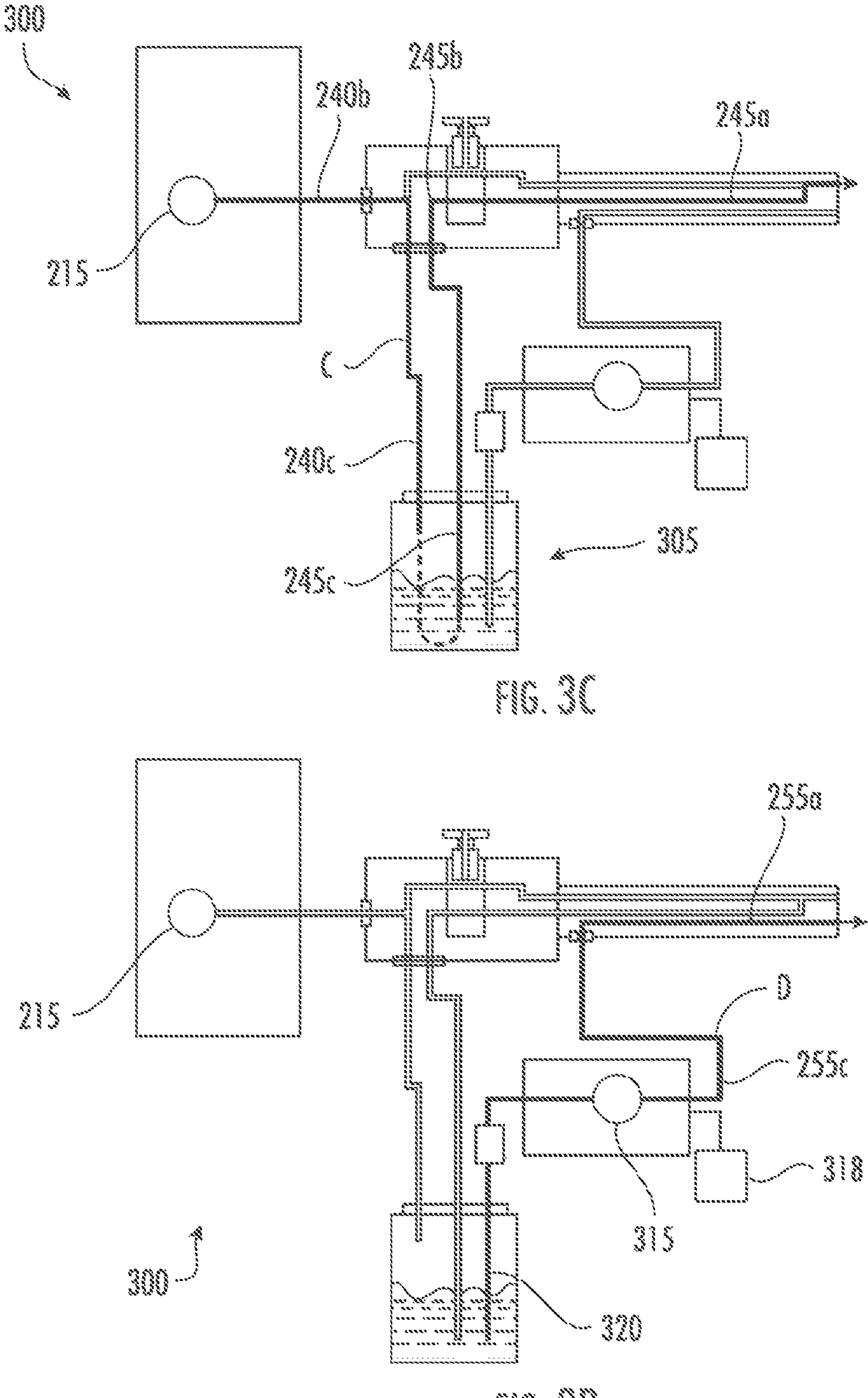
FIG. 3C depicts the endoscope system of FIG. 3A, wherein the system is activated to deliver lens wash fluid through the patient end of the endoscope.
FIG. 3D depicts the endoscope system of FIG. 3A, wherein the system is activated to deliver irrigation fluid through the patient end of the endoscope.

As shown in FIG. 3C, the endoscope 100 is in a lens wash delivery state with the gas/water valve 140 in a second position. When lens wash is called for at the distal tip 100*c*, for example, to clean the end face 100*d* of the distal tip 100*c*, the user, keeping the vent hole in the air/water valve closed off, depresses the valve 140 to its furthest point in the valve well 135. The second position blocks off the gas supply to both atmosphere and the gas supply line 240*a* in the endoscope, and opens up the gas/water valve 140 to allow lens wash water to pass through to the lens wash supply line 245*a* in the endoscope shaft 100*a* and out the gas/lens wash nozzle 220 at the distal tip 100*c*. In this state, gas (pressure) is delivered along path C from the air pump 215, through the branched line in the connector portion 265 and out of the gas supply tubing 240*c* to the water reservoir 305. The gas (pressure) pressurizes the surface of the remaining water 285 in the reservoir 305 and pushes water up the lens wash supply tube 245*c* to the connector portion 265. The pressurized lens wash water is pushed further through the lens wash feed line 245*b* in the umbilical 260 and through the gas/water valve 140. Since the system 300 is closed, gas pressure is allowed to build and maintain a calibrated pressure level in the water reservoir 305, rather than venting to atmosphere or being delivered to the patient. This pressure, along with the endoscope feed and supply lines and external tubing, translates to a certain range of flow rate of the lens wash.

As shown in FIG. 3D, the endoscope 100 is in an irrigation delivery state. This may be performed at the same or a different time from the delivery of gas and/or lens wash. When irrigation is called for at the distal tip 100*c*, for example, if visibility in the treatment area is poor or blocked by debris, or the like, the user activates the irrigation pump 315 (e.g., by depressing foot switch 318) to delivery water along path D. With the pump 315 activated, water is sucked out of the water reservoir 305 through the upstream irrigation supply tubing 320 and pumped along the downstream irrigation supply tubing 255*c* to the connector portion 265. The irrigation pump head pressure pushes the irrigation water further through the irrigation feed line 255*b* in the umbilical 260, through the irrigation supply line 255*a* in the endoscope shaft 100*a*, and out the irrigation opening 225 at the distal tip 100*c*. The irrigation pump pressure may be calibrated, along with the endoscope irrigation feed and supply lines and external tubing, to deliver a certain range of flow rate of the irrigation fluid.

Figure 4:
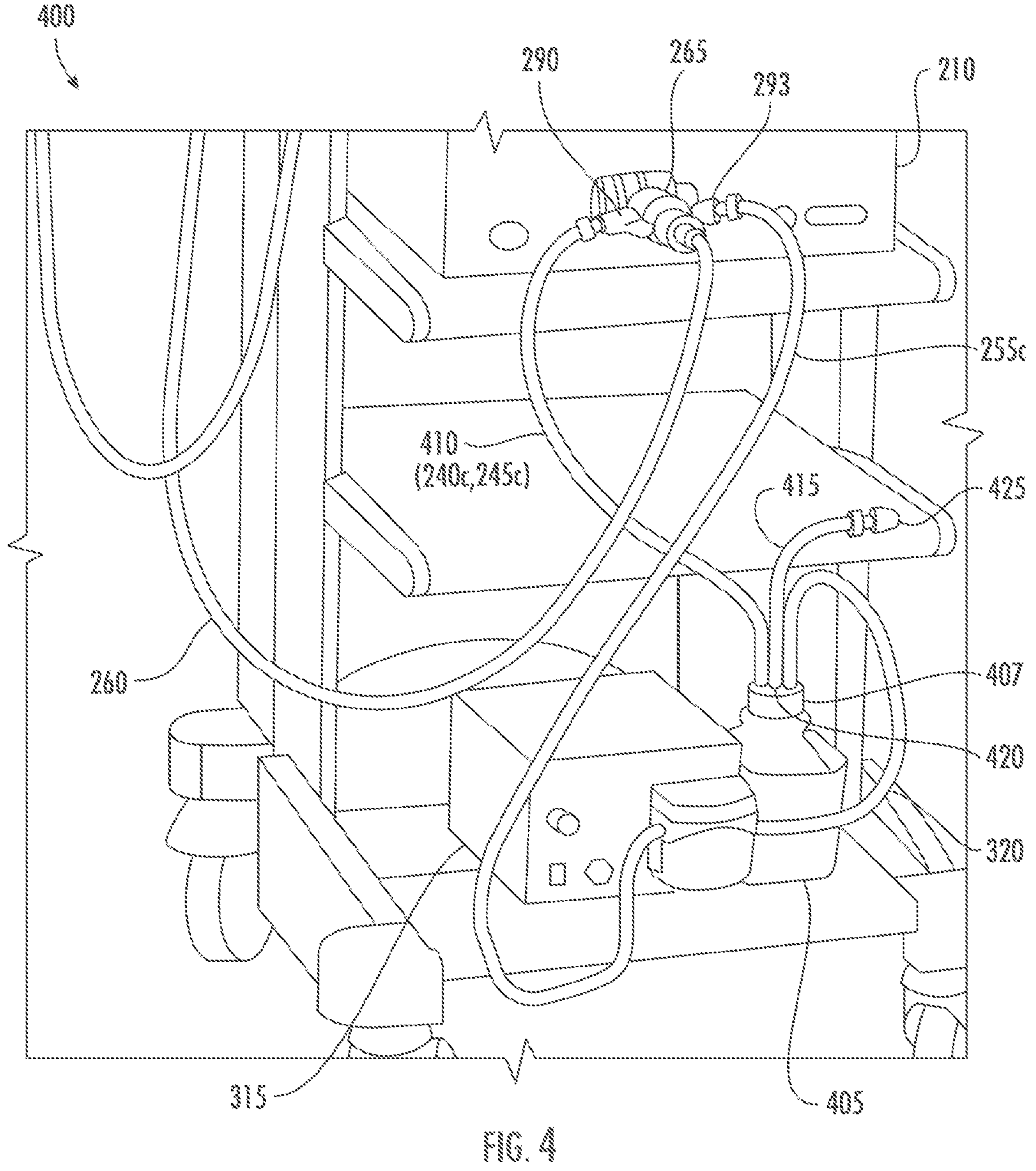
FIG. 4 depicts a hybrid endoscope system including a video processing unit, connector portion, peristaltic irrigation pump, water reservoir and top, coaxial gas and lens wash supply tubing, upstream and downstream irrigation supply tubing, and alternative gas supply tubing.

FIG. 4 is a schematic drawing illustrating a further embodiment of a hybrid system 400 including a video processing unit 210, connector portion 265, peristaltic irrigation pump 315, water reservoir 405 and top 407, coaxial gas and lens wash supply tubing 410, upstream and downstream irrigation supply tubing 320, 255*c*, respectively, and alternative gas (e.g., $CO_2$) supply tubing 415. A length of the alternative gas supply tubing 415 passes from one end positioned in the gas gap 275 (see FIG. 2) between the top 407 of the water reservoir 405 and the remaining water 285 in the reservoir through an additional opening 420 in the top of the reservoir to a detachable connection 425 for a source of the alternative gas supply (e.g., $CO_2$ hospital house gas source). When the alternative gas supply is desired, such as $CO_2$ gas, the air pump 215 on the video processing unit 210 may be turned off and $CO_2$ gas, rather than air, is thereby flowed to the water reservoir 405 pressurizing the water surface. Generally, the flow of $CO_2$ through the endoscope 100 is similar to the flow of air. In the neutral state, $CO_2$ gas flows backward up the gas supply tubing 240*c* to the connector portion 265, up the gas feed line 240*b*, and is vented through the gas/water valve 140 to atmosphere. In the first position, the user closes off the vent hole in the gas/water valve 140, and the $CO_2$ gas is flowed through the gas/water valve to the gas supply line 240*a* in the endoscope shaft 100*a* and out the gas/lens wash nozzle 220 at the distal tip 100*c*. In the second position, the user depresses the valve 140 to the bottom of the valve well 135, keeping the vent hole in the gas/water valve closed off. The second position blocks the $CO_2$ gas supply to both atmosphere and the gas supply line 240*a* in the endoscope 100, and opens up the gas/water valve 140 to allow lens wash water to pass through to the lens wash supply line 245*a* in the endoscope shaft 100*a* and out the gas/lens wash nozzle 220 at the distal tip 100*c*. Gas (pressure) in the reservoir 405 is maintained by delivery gas through alternative gas (e.g., $CO_2$) supply tubing 415. The irrigation function may be accomplished in a similar manner as the operation described above with respect to FIG. 3D.

Figure 5A:
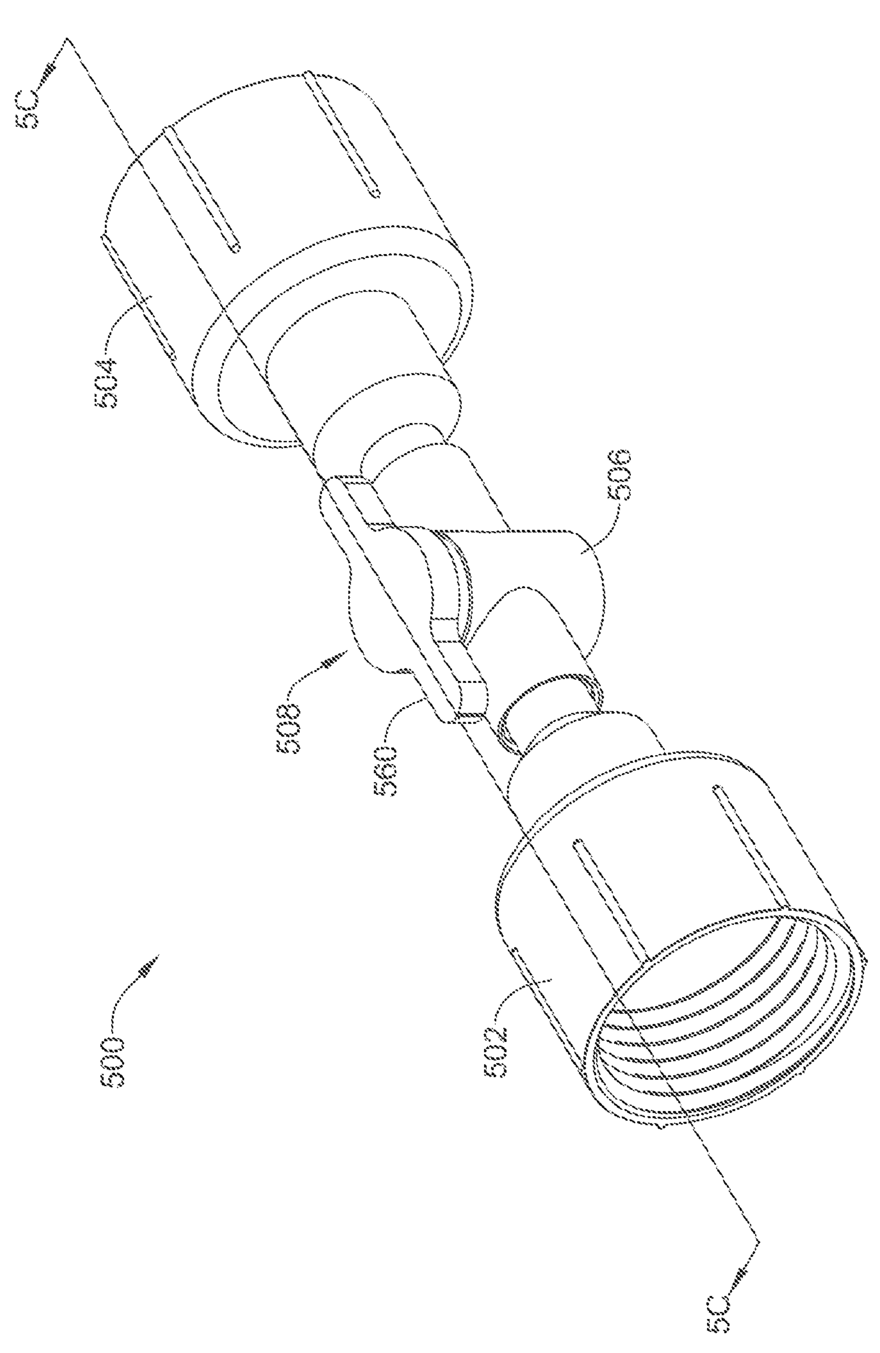
FIG. 5A depicts a perspective view of an illustrative fitting for refilling a refillable fluid reservoir in an open configuration.
Figure 5B:
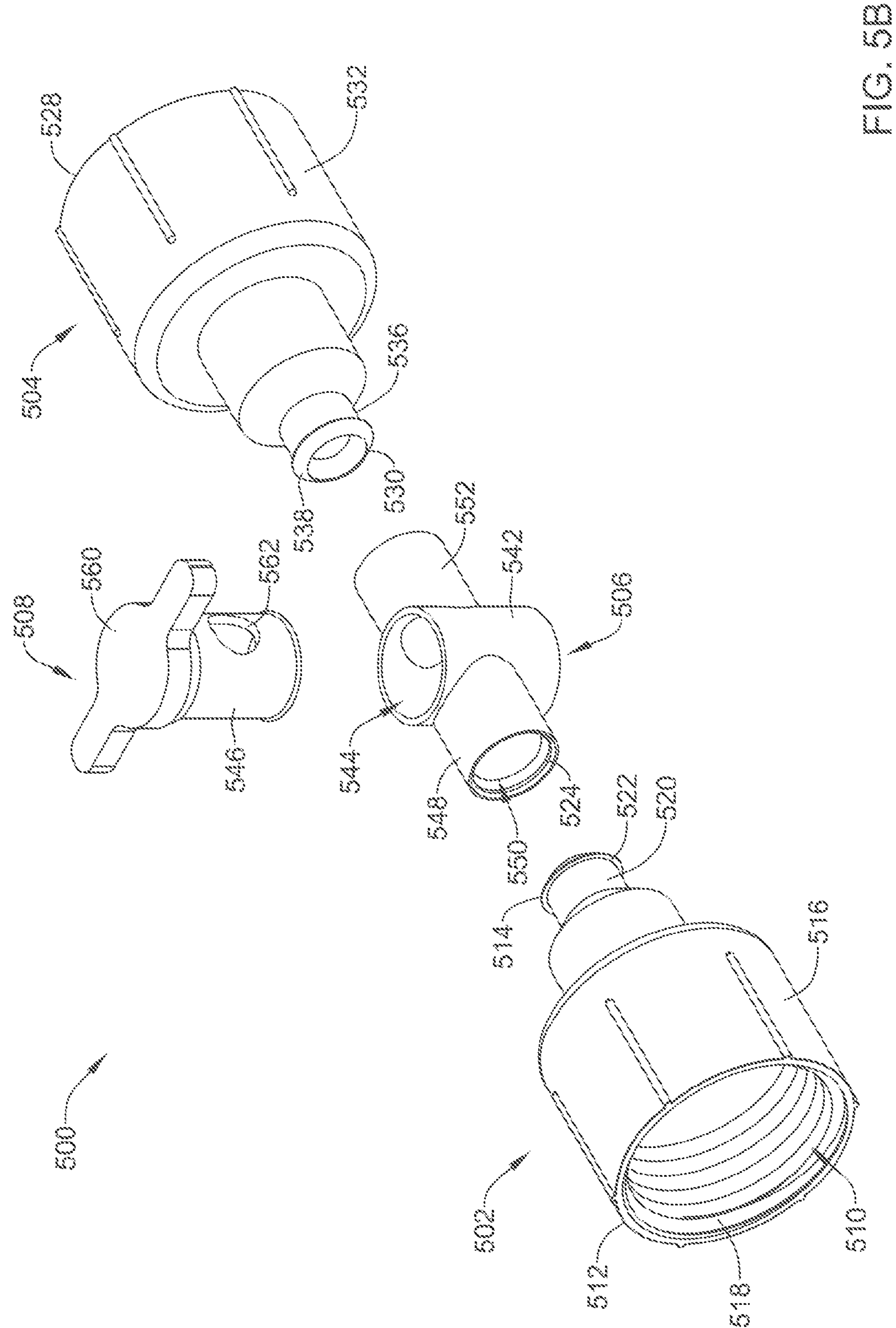
FIG. 5B depicts an exploded perspective view of the illustrative fitting of FIG. 5A.
Figure 5C:
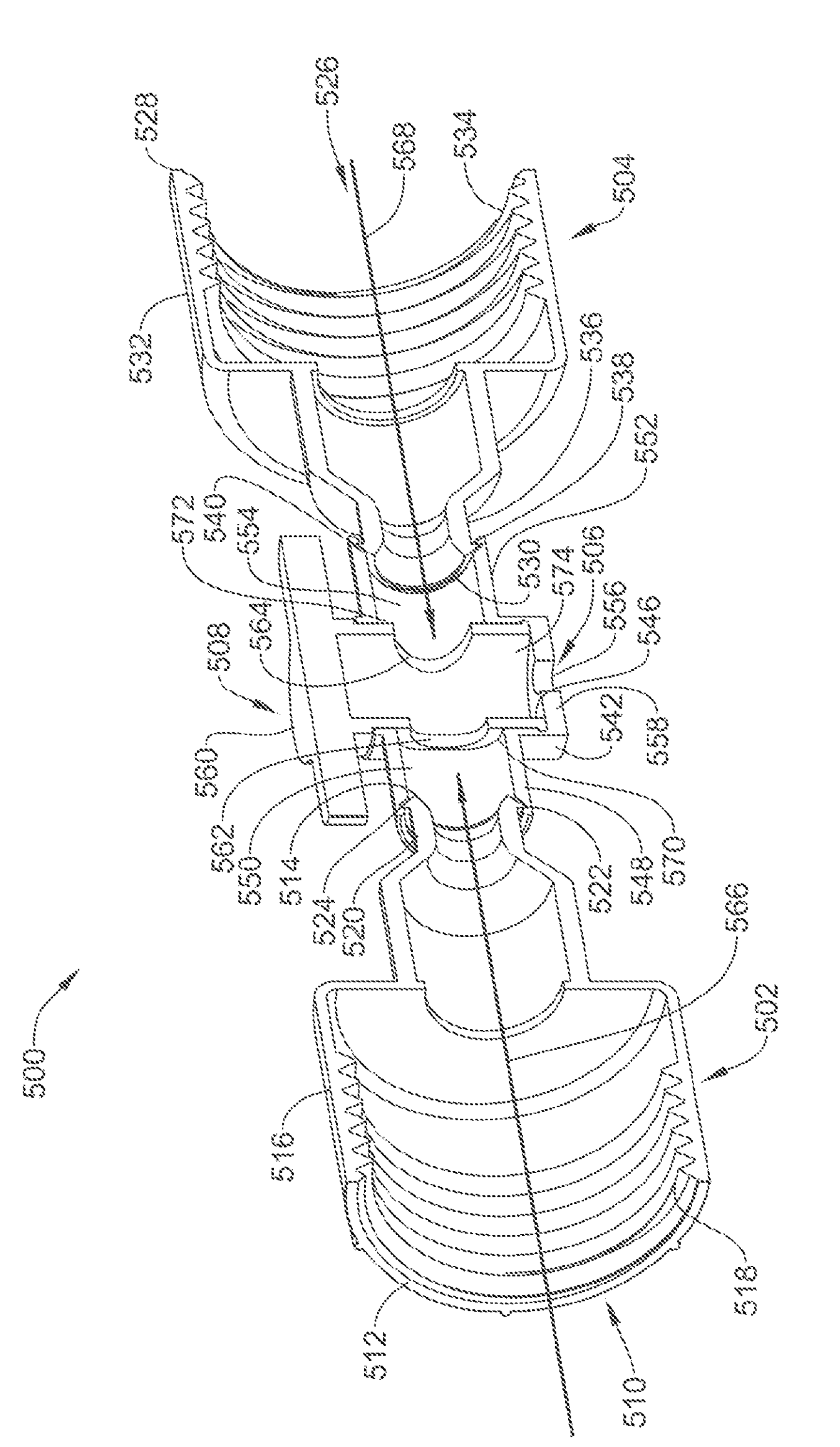
FIG. 5C depicts a schematic cross-sectional view of the fitting of FIG. 5A, taken at line 5C-5C.
Figure 5D:
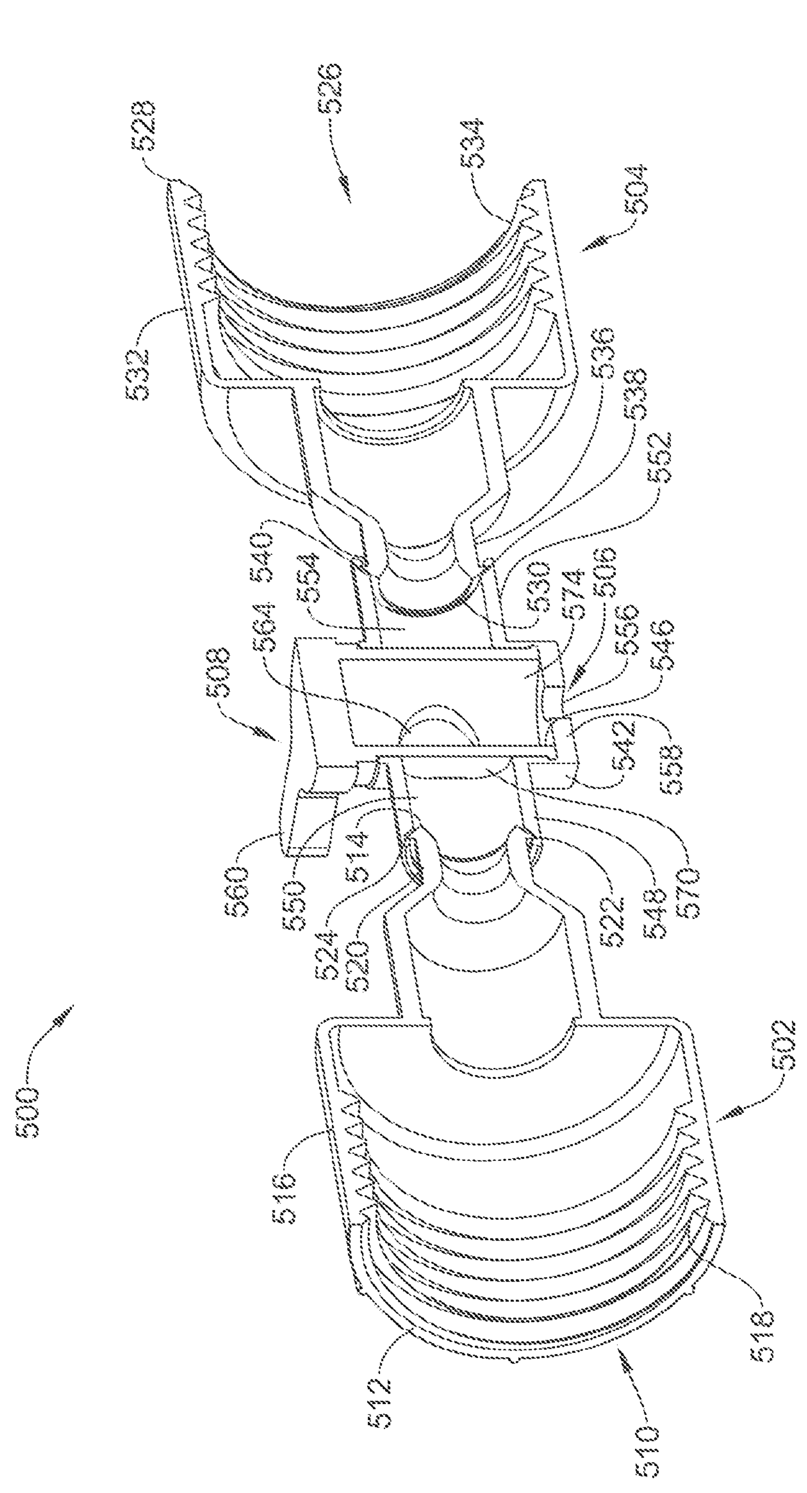
FIG. 5D depicts a schematic cross-sectional view of the fitting of FIG. 5A in a closed configuration.

As described above, it may be desirable to reduce opportunities for contamination to the tube set 240*c*, 245*c*, 320, 410, 415 during replacement of the water reservoir by providing a refillable water reservoir 270, 305, 405. FIGS. 5A-5D depict various views of an illustrative fitting 500 to facilitate filling and/or refilling the water reservoir 270, 305, 405. FIG. 5A depicts a perspective view of an illustrative fitting 500 in an open configuration. FIG. 5B depicts an exploded perspective view of the illustrative fitting 500 of FIG. 5A. FIG. 5C depicts a cross-sectional view of the illustrative fitting 500 of FIG. 5A, taken at line 5C-5C of FIG. 5A. FIG. 5D is a cross-sectional view of the fitting 500 of FIG. 5A in a closed configuration. Generally, the fitting 500 may include a first coupling portion 502, a second coupling portion 504, a connecting member 506, and a valve actuator 508. The connecting member 506 and the valve actuator 508 may be disposed between the first coupling portion 502 and the second coupling portion 504.

The first coupling portion 502 may define a lumen 510 extending from a first end 512 to a second end 514 thereof. The lumen 510 may be in selective fluid communication with the connecting member 506 through actuation of the valve actuator 508. For example, when the valve actuator 508 is in the open configuration, the lumen 510 is in fluid communication with the connecting member 506 and when the valve actuator 508 is in the closed configuration, the lumen 510 is fluidly isolated from a fluid outlet 556 of the connecting member 506. A first coupling member 516 may be disposed adjacent to the first end 512 of the first coupling portion 502. The first coupling member 516 may define a plurality of internal threads 518 for engaging mating external threads on a water bottle (not explicitly shown). A second coupling member 520 may be disposed adjacent to the second end 514 of the first coupling portion 502. The second coupling member 520 may include a circumferentially extending raised ridge or protrusion 522. The raised ridge 522 may be configured to engage a mating recess 524 formed in an inner surface of the connecting member 506. It is contemplated that raised ridge 522 may include features, such as, but not limited to, tapered surfaces, to facilitate assembly of the first coupling portion 502 with the connecting member 506 while inhibiting accidental disassembly. The second coupling member 520 may have a diameter that is less than a diameter of the first coupling member 516. However, this is not required. In some instances, the second coupling member 520 may have a diameter that is similar to, the same as, or greater than a diameter of the first coupling member 516. Further, while the first coupling member 516 and the second coupling member 520 are shown as extending colinearly or along a same axis, in some cases, the first coupling member 516 may be positioned at a non-parallel angle to the second coupling member 520. For example, the first coupling member 516 may be positioned such that a longitudinal axis thereof is generally orthogonal to a longitudinal axis of the second coupling member 520. This is just one example. Other configurations or arrangements may be used, as desired.

The second coupling portion 504 may define a lumen 526 extending from a first end 528 to a second end 530 thereof. The lumen 526 may be in selective fluid communication with the connecting member 506 through actuation of the valve actuator 508. For example, when the valve actuator 508 is in the open configuration, the lumen 526 is in fluid communication with the connecting member 506 and when the valve actuator 508 is in the closed configuration, the lumen 526 is fluidly isolated from a fluid outlet 556 of the connecting member 506. A first coupling member 532 may be disposed adjacent to the first end 528 of the second coupling portion 504. The first coupling member 532 may define a plurality of internal threads 534 for engaging mating external threads on a water bottle (not explicitly shown). A second coupling member 536 may be disposed adjacent to the second end 530 of the second coupling portion 504. The second coupling member 536 may include a circumferentially extending raised ridge or protrusion 538. The raised ridge 538 may be configured to engage a mating recess 540 formed in an inner surface of the connecting member 506. It is contemplated that raised ridge 538 may include features, such as, but not limited to, tapered surfaces, to facilitate assembly of the second coupling portion 504 with the connecting member 506 while inhibiting accidental disassembly. The second coupling member 536 may have a diameter that is less than a diameter of the first coupling member 532. However, this is not required. In some instances, the second coupling member 536 may have a diameter that is similar to, the same as, or greater than a diameter of the first coupling member 532. Further, while the first coupling member 532 and the second coupling member 536 are shown as extending colinearly or along a same axis, in some cases, the first coupling member 532 may be positioned at a non-parallel angle to the second coupling member 536. For example, the first coupling member 532 may be positioned such that a longitudinal axis thereof is generally orthogonal to a longitudinal axis of the second coupling member 536. This is just one example. Other configurations or arrangements may be used, as desired.

The connecting member 506 may include a central body portion 542 defining a cavity 544 therein and extending along a first axis. The cavity 544 may be generally cylindrical to receive a mating valve body 546 of the valve actuator 508. Together, the connecting member 506 and the valve actuator 508 may function as or form an actuatable valve. It is contemplated that the cavity 544 may take other shapes to accommodate different structures of the valve actuator 508. A first tubular member 548 defining a lumen 550 may extend from an opening 570 in the side wall of the central body portion 542. The lumen 550 may fluidly couple the lumen 510 of the first coupling portion 502 with the cavity 544 of the connecting member 506. A second tubular member 552 defining a lumen 554 may extend from an opening 572 in the side wall of the central body portion 542 in a direction opposite from the first tubular member 548. The lumen 554 may fluidly couple the lumen 526 of the second coupling portion 504 with the cavity 544 of the connecting member 506. The lumens 550, 554 may extend along a second axis that is generally orthogonal to the first axis of the central body portion 542. The first tubular member 548 and the second tubular member 552 may be spaced approximately 180° from one another such that the share a common axis. However, this is not required. The first tubular member 548 and the second tubular member 552 may be spaced more than 180° or less than 180°, as desired. It is contemplated that the connecting member 506 may be structured to accommodate more than two coupling portions 502, 504. In such an instance, the first tubular member 548, the second tubular member 552, and any additional member tubular members may be spaced less than 180° from one another. A fluid outlet 556 may be formed through an end surface 558 of the connecting member 506. The fluid outlet 556 may be disposed between the first coupling portion 502 and the second coupling portion 504 and in selective fluid communication with the lumens 510, 526 of the first coupling portion 502 and the 504 to transfer a fluid from the water bottles to a water reservoir, as will be described in more detail herein. In some embodiments, the fluid outlet 556 may be formed in a plane generally orthogonal to a plane of the lumens 510, 526, although this is not required. Other configurations may be used as desired.

The valve actuator 508 may include an actuation member 560 and a valve body 546. In some embodiments, the valve actuator 508 may be a stopcock. Other actuatable valves, such as, but not limited to, gate valves, ball valves, butterfly valves, globe valves, etc. may be used, as desired. The valve actuator 508 may include an actuation member 560, such as, but not limited to, a handle, lever, hand wheel, etc. In the illustrated embodiment, the actuation member 560 may be rotated to move the valve actuator 508 between an open configuration and a closed configuration. For example, the actuation member 560 may be rotated by about 90° to move the valve body 546 between an open configuration and a closed configuration. In some embodiments, the actuation member 560 may be rotated by less than 90° to partially open or partially close the valve actuator 508. It is contemplated that the amount of rotation required to open and/or close the valve actuator 508 may be determined by an internal structure of the valve actuator 508. In some examples, the actuation member 52 may be rotated more than 90° or less than 90°. It is further contemplated that the actuation member 560 may be structured to impart a linear force on the actuatable valve (e.g., a sliding motion).

The valve body 546 may be configured to be disposed within the cavity 544 of the connecting member 506 and may be generally tubular to facilitate rotation of the valve actuator 508 therein. However, other shapes may be used depending on the valve type and/or actuation member 560 used for the valve actuator 508. The valve body 546 may include a first aperture 562 configured to be in selective fluid communication with the lumen 510 of the first coupling portion 502 and a second aperture 564 configured to be in selective fluid communication with the lumen 526 of the second coupling portion 504 as well as an internal cavity 574 of the valve body 546. For example, when the valve actuator 508 is in the open configuration, the first aperture is aligned with lumen 510 of the first coupling portion 502 and the second aperture 564 is aligned with the lumen 526 of the second coupling portion 504. When a water bottle is coupled to the first coupling portion 502 and the valve actuator 508 is opened, fluid or water may flow from the water bottle, through the lumen 510, and into the cavity 574 along first flow path 566. The fluid may then exit the cavity 574 via the fluid outlet 556. Similarly, when a water bottle is coupled to the second coupling portion 504 and the valve actuator 508 is opened, fluid or water may flow from the water bottle, through the lumen 526, and into the cavity 574 along a second fluid flow path 568. The fluid may then exit the cavity 574 via the fluid outlet 556. The fluid outlet 556 may be disposed in a plane generally orthogonal to a plane of the first and second fluid paths 566, 568. To stop a flow of fluid from entering the cavity 574 from the fluid paths 566, 568, the valve actuator 508 is actuated to the closed configuration.

To fill a fluid reservoir (such as reservoirs 270, 305, 405), the valve actuator 508 may be moved to the closed configuration (FIG. 5D). In the closed configuration, the solid side wall of the valve body 546 is aligned with the openings 570, 572 in the connecting member 506 to fluidly isolate the lumens 510, 526 from the cavity 544 and the fluid outlet 556. With the valve actuator 508 in the closed configuration, one or both of the first and second coupling portions 502, 504 are then coupled to a water bottle. For example, a water bottle may be coupled to each coupling portion 502, 504 if so desired. It is contemplated that maintaining the valve actuator 508 in the closed configuration during coupling of the water bottle(s) may allow more than one water bottle to be coupled without spilling water. Once the water bottle(s) have been coupled to the first and/or second coupling portions 502, 504, the fluid outlet 556 may be aligned with an opening or port in the fluid reservoir and the valve actuator 508 opened. In some cases, a tube or other flow directing mechanism may be used to direct a flow of fluid from the fluid outlet 556 to the fluid reservoir. Fluid may then flow from the water bottles, along the first and/or second flow paths 566, 568 to the cavity 574, through the fluid outlet 556, and into the reservoir. In some cases, the user may tip or slant the fitting 500 to allow water to flow from one water bottle before tipping or slanting the fitting in an opposite direction to allow water to flow from the other water bottle.

Figure 6:
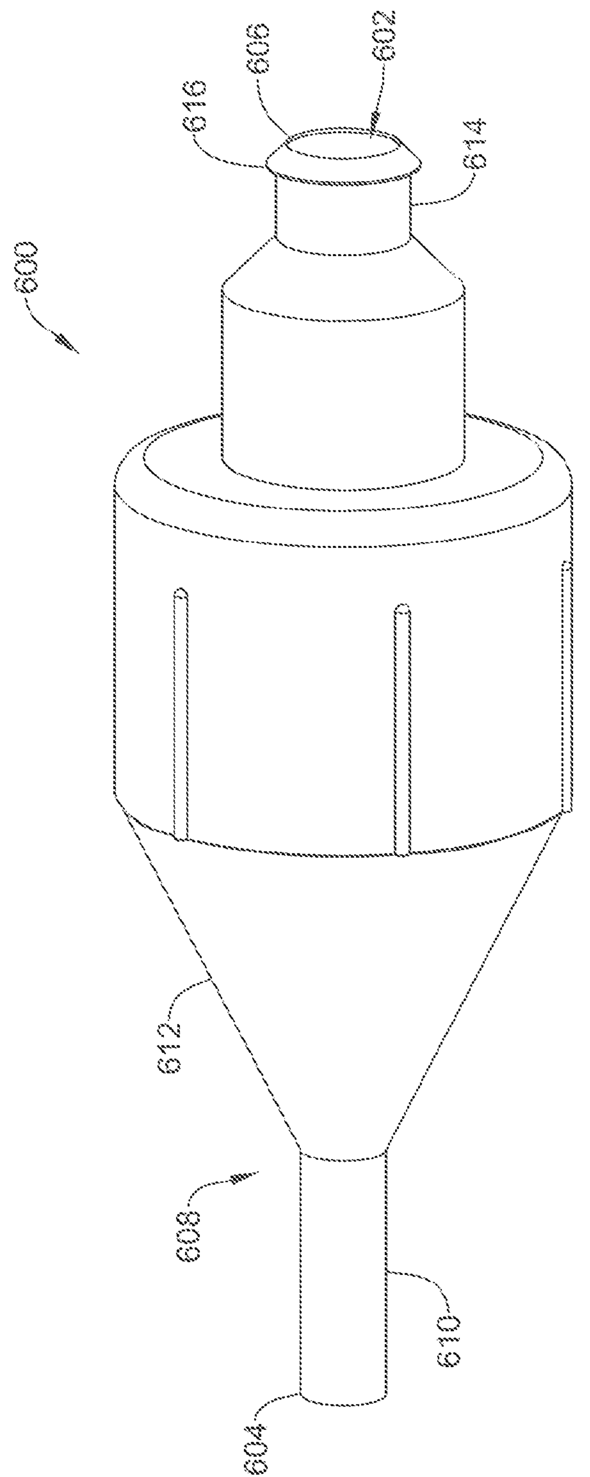
FIG. 6 depicts a perspective view of another illustrative coupling portion that may be used with the fitting of FIGS. 5A-5D.

While the fitting 500 is illustrated as including threaded coupling portions 502, 504 for coupling the fitting 500 to a water bottle, it is contemplated that other coupling mechanisms may be used, as desired. FIG. 6 depicts a perspective view of another illustrative coupling portion 600 that may be used in place of one or both of the first and second coupling portions 502, 504 to couple the fitting to a water bottle. The coupling portion 600 may define a lumen 602 extending from a first end 604 to a second end 606 thereof. The lumen 602 may be in selective fluid communication with the connecting member 506 through actuation of the valve actuator 508. For example, when the valve actuator 508 is in the open configuration, the lumen 602 is in fluid communication with the connecting member 506 and when the valve actuator 508 is in the closed configuration, the lumen 602 is fluidly isolated from the connecting member 506. A first coupling member 608 may be disposed adjacent to the first end 604 of the coupling portion 600. The first coupling member 608 may include a piercing tip 610, such as, but not limited to, a blunt or sharpened needle tip, for puncturing a spikable or pierceable cap of a water bottle. The piercing tip 610 may extend from a conical region 612 configured to engage the mouth of the water bottle to provide a fluid tight seal between the coupling member 608 and the water bottle. It is contemplated that piercing the water bottle cap may allow for coupling of the fitting 500 to the water bottle without having to unscrew the cap which allows atmospheric air to enter (which may potentially contaminate the water). A second coupling member 614 may be disposed adjacent to the second end 606 of the coupling portion 600. The second coupling member 614 may include a circumferentially extending raised ridge or protrusion 616. The raised ridge 616 may be configured to engage a mating recess 524 formed in an inner surface of the connecting member 506. It is contemplated that raised ridge 616 may include features, such as, but not limited to, tapered surfaces, to facilitate assembly of the first coupling portion 502 with the connecting member 506 while inhibiting accidental disassembly. The second coupling member 614 may have a diameter that is less than a diameter of the first coupling member 608. However, this is not required. In some instances, the second coupling member 614 may have a diameter that is similar to, the same as, or greater than a diameter of the first coupling member 608. Further, while the first coupling member 608 and the second coupling member 614 are shown as extending colinearly or along a same axis, in some cases, the first coupling member 608 may be positioned at a non-parallel angle to the second coupling member 614. For example, the first coupling member 608 may be positioned such that a longitudinal axis thereof is generally orthogonal to a longitudinal axis of the second coupling member 614. This is just one example. Other configurations or arrangements may be used, as desired.

Figure 7:
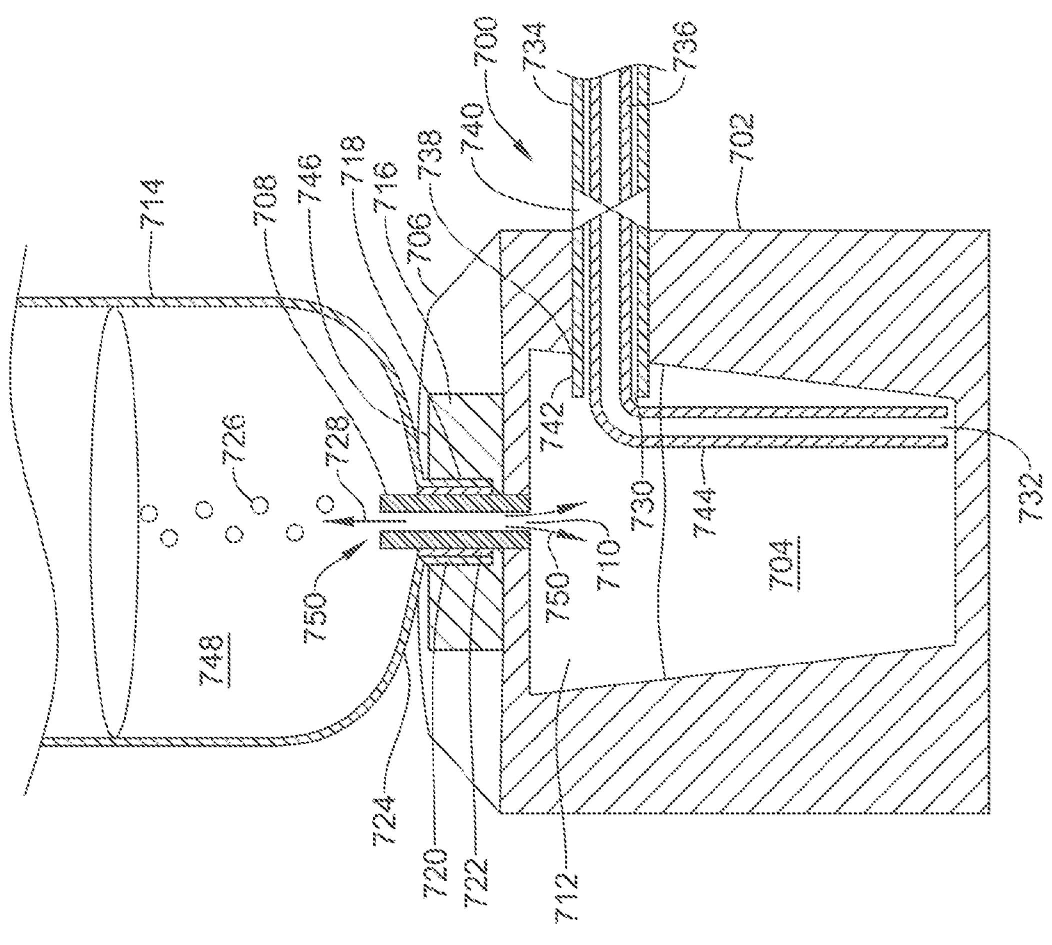
FIG. 7 depicts a cross-sectional view of another illustrative refillable fluid reservoir.

FIG. 7 depicts a cross-sectional view of another illustrative refillable fluid reservoir 700. The reservoir 700 may be configured to be used in an endoscopic system and includes components similar to the endoscope and endoscope systems described with regard to FIGS. 1-4; however, not all features may be described or shown here if not pertinent to the fluid circuit of the system. The reservoir 700 includes a container 702 configured to hold a fluid 704. In some embodiments, the container 702 may be configured to hold in the range of about 0.5 liters (L) to about 20 L of fluid. However, the container 702 may be configured to hold less than 0.5 L or more than 20 L if so desired. For example, in some cases, the container 702 may be configured to hold in the range of 1 to 15 L, in the range of about 3 L to about 10 L, in the range of about 5 L to about 8 L, etc.

Generally, the container 702 may be refilled by positioning a water bottle 714 upside down at an inlet port and air 726 is allowed to flow, as shown at 728, into the water bottle 714. The air causes the water 748 to flow, as shown at 750, into the container 702. In some embodiments, the water bottle 714 may be a standard 1 L water bottle. In other embodiments, the water bottle 714 may have a volume greater than 1 L, such as, but not limited to, 5 L, 10 L, or more. For example, in some cases, the water bottle 714 may be configured to supply water to the container 702 in sufficient quantity that the water bottle 714 continually supplies water to the container 702 for more than one endoscopic procedure. For example, the container 702 may not need refilled and/or the water bottle 714 does not need replaced for more than one endoscopic procedure or throughout a day of endoscopic procedures.

The container 702 extends from a first or distal end 706 to a second or proximal end 707. A reduced diameter stem or tubular port 708 may extend away from the first end 706 in a direction opposite the second end 707 of the container 702. Generally, the tubular port 708 may be a hollow cylindrical stem in fluid communication with an opening 710 of the container 702 and configured to selectively provide a fluid coupling between an exterior of the container 702 and an interior 712 of the container 702 to allow fluid 704 to be transferred into the container 702 from a water bottle 714. The tubular port 708 may be formed as a single monolithic structure with the container 702 or a separate component, as desired. The tubular port 708 may have a diameter, or cross-sectional dimension, that is less than a diameter, or cross-sectional dimension of the first end 706 or second end 707 of the container 702. In some cases, the tubular port 708 may have a generally cylindrical shape while the container 702 may have a generally rectangular prism shape. However, this is not required. The container 702 and/or tubular port 708 may take any shape desired.

In some embodiments, an optional support block 716 may extend away from the first end 706 in a direction opposite the second end 707 of the container 702. The support block 716 may define an opening 718 extending through a thickness thereof. The opening 718 may be sized and shaped to receive a neck 720 of the water bottle 714 and/or the tubular port 708 of the container 702. For example, the tubular port 708 may extend through the opening 718 in the support block 716. When the water bottle 714 is engaged with the reservoir 700, the neck 720 of the water bottle 714 may be disposed within an annular space 722 between an inner wall of the opening 718 and an outer surface of the tubular port 708. An upper edge 724 of the water bottle 714 may engage an upper surface 746 of the support block 716 to maintain the water bottle 714 in an inverted orientation.

The reservoir 700 may include a gas inlet 730 and a water outlet 732 for coupling to a gas supply and a water supply tube. In some embodiments, the gas inlet 730 and/or water outlet 732 may be one or more ports for coupling separately provided gas supply lines and/or water supply lines. In other embodiments, the gas inlet 730 and/or water outlet 732 may be a part of a gas supply tubing 734 or water supply tubing 736. For example, reservoir 700 may be connected in fluid communication with a gas supply/alternate gas supply tubing (or gas supply tubing) 734 and a lens wash supply/irrigation supply tubing (or water supply tubing) 736. The gas supply tubing 734 extends from a second end external to the reservoir 700 through a reservoir opening 738 at or adjacent the first end 706 of the container 702. The shared gas supply tubing 734 may terminate within a reservoir gap, at or below the opening 738, but not extending into the remaining fluid 704 in the container 702 as shown. However, in some cases, the gas supply tubing 734 may extend into the fluid 704. For example, the opening 738 may be at a bottom or side of the container 702 such that the shared gas supply tubing 734 terminates within the fluid with gas bubbling up through the fluid 704 to pressurize the container 702. A lumen extends through the gas supply tubing 734 for receiving a flow of air and/or gas therethrough. The lumen of the gas supply tubing 734 is in operative fluid communication with an interior of the reservoir 700. The water supply tubing 736 extends from a second end external to the reservoir 700 through the reservoir opening 738, terminating in a first end within the remaining fluid 704 at or substantially at the bottom of the container 702. In some embodiments, the water supply tubing 736 may terminate at the opening 738. For example, when the opening 738 is at or adjacent to the second end 707 of the container 702, a dip tube may not be required. A lumen extends through the water supply tubing 736 for receiving a flow of fluid therethrough. The lumen of the lens wash supply/irrigation supply tubing 736 is in selective operative fluid communication with the bottom portion of the container 702. In the illustrated embodiment, the gas supply tubing 734 and the water supply tubing 736 may enter the container 702 through a single or common opening 738. For example, the gas supply tubing 734 and the water supply tubing 736 may be coaxially arranged as shown. However, this is not required. In some cases, the gas supply tubing 734 and the water supply tubing 736 may extend in a side-by-side arrangement or may be separately connected to the container 702 in different locations. The opening 738 may include a grommet, heat seal, or other sealing mechanism configured to seal the container 702 about the tubing 734, 736 in a fluid and pressure tight manner thereby allowing the reservoir to be pressurized. Moreover, the tubular port 708 may be provided with a valve (not shown) thereby allowing the container 702 to be isolated from the water bottle 714, except during periodic filling periods when the water bottle 714 us used to fill the container 702.

A portion of a gas supply tubing 734 and a portion of lens wash supply tubing 736 may extend from the reservoir 700, respectively, and may be connected in fluid communication with the endoscope at gas/lens wash connection on the connector portion 265 of the umbilical. The gas supply tubing 734 is connected in fluid communication with a gas pump (not explicitly shown) and/or gas feed line (not explicitly shown), and the lens wash supply tubing 736 is connected in fluid communication with lens wash feed line (not explicitly shown), within connector portion 265. While not explicitly shown, irrigation supply tubing may be coupled to the water supply tubing 736 via a manifold to supply irrigation fluid from the reservoir 700 or a separate irrigation supply tubing may be provided. For example, irrigation supply tubing (not shown) may extend from a second end external to the reservoir 700 through a reservoir opening (not shown), terminating in a first end within the remaining fluid 704 at or substantially at the bottom of the container 702.

It is contemplated that the reservoir 700 may be filled and refilled as needed by inverting a water bottle 714 and positioning it over the tubular port 708. In some embodiments, the water bottle 714 may include a pierceable cap (see, for example FIGS. 8A and 8B) such that a watertight seal is maintained as the water bottle 714 is inverted. It is contemplated the tubular port 708 may puncture or pierce the cap of the water bottle 714 to allow a flow of fluid therethrough. The refilling of the reservoir 700 may be performed during a procedure or between procedures, as necessary. The water may be sterile or non-sterile, as desired. For example, sterile water may be used for therapeutic procedures while non-sterile water may be used for diagnostic procedures. As the external surfaces of the tubular port 708 are non-sterile, prior to filling/refilling and subsequent contact with sterile water, the exterior may be wiped down with a disinfecting agent. It is contemplated that refilling the reservoir 700 with sterile or non-sterile water may create more flexibility and reduce the need to have as much sterile water in storage. Further, refilling the reservoir 700 via the tubular port 708 may also remove the need to disconnect the reservoir 700 from the tubing 734, 736 throughout the day eliminating or greatly reducing the possibility of cross contamination by removing the need to replace the water container.

To fill the container 702, a neck 720 of a water bottle 714 is placed on or over the tubular port 708. In the illustrated embodiment, the neck 720 of the water bottle 714 is placed over the tubular port 708. The tubular port 708 may be sized and shaped to form a fluid tight seal with the neck 720 of the water bottle 714. However, this is not required. Water flows down into the container 702 along flow path 750 while air moves up into the water bottle 714 along flow path 728. When the water bottle 714 is empty and/or when the container 702 is filled to the desired amount, the water bottle 714 may be removed. In some cases, more than one water bottle 714 may be used to fill the container 702.

In some embodiments, the water bottle 714 may be configured to remain assembled with the reservoir 700 during the endoscopic procedure. In other embodiments, the water bottle 714 may be removed from the reservoir 700 and a cap or plug (not explicitly shown) positioned over and/or within the opening of the tubular port 708 and/or the opening 718 of the support block 716.

When the water bottle 714 is configured to remain assembled with the reservoir 700 and provide enough water for more than one procedure, it is contemplated that a reservoir 700 may be a free-standing unit provided in each procedure suite. For example, the reservoir 700 may be configured to remain in the procedure suite. In other examples, the reservoir 700 may be provided in a room adjacent to the procedure suite with the tubing passing through into the procedure suite. It is contemplated that large volume (e.g., greater than 1 L) water bottles 714 may be provided to the medical center pre-filled and can be stored as necessary. Alternatively, or additionally, some water bottles 714 may be filled at the medical center. It is contemplated that the reservoir 700 may include filtration and/or sterilization capabilities to ensure the water is safe to be used in procedures. Some suitable sterilization techniques may include, but are not limited to, ultraviolet light, heat, chemical sterilization, etc. Single use tubing (e.g., gas supply tubing 734, lens wash supply tubing 736, irrigation tubing) may be coupled to the reservoir 700 at a port. For example, the reservoir 700 may include a valve 740 (such as, but not limited to, a stopcock, a ball valve, a gate valve, a butterfly valve, a globe valve, etc.) or other connections (such as, but not limited to, a quick-connect) that selectively fluidly couples the gas supply tubing 734, lens wash supply tubing 736, and/or irrigation tubing with corresponding gas tubing 742 and lens wash tubing 744 within the interior 712 of the container 702. The valve 740 may be open during use of the endoscope and closed when the system is not in use to maintain sterility of the system. The valve 740 or other connection may be manually operated by the user or automatically actuated via a computer control system.

Figure 8B:
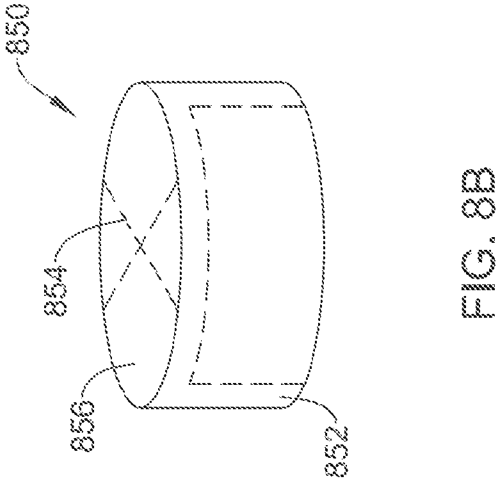
FIG. 8B depicts a perspective view of another illustrative puncturable cap.
Figure 8A:
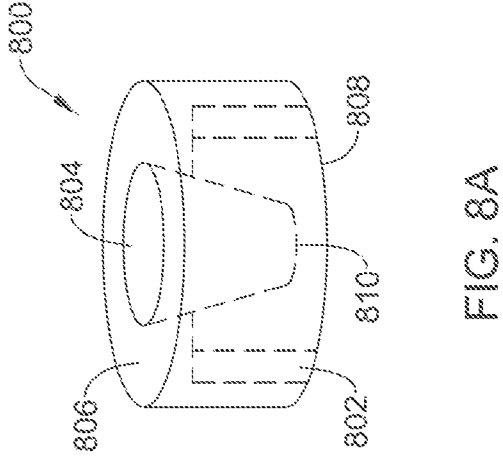
FIG. 8A depicts a perspective view of an illustrative puncturable cap.

FIG. 8A depicts a perspective view of an illustrative puncturable cap 800. The cap 800 may be configured to be secured to a mouth of the water bottle 714. For example, the cap 800 may include an annular slot 802 configured to receive the mouth of the water bottle 714 therein. The cap 800 may be configured to form a snap fit or threadably engage the water bottle 714. Other mechanical engagements may be used, as desired. The cap 800 may further include a recess or indent 804 formed in a top surface 806 of the cap 800 and extending towards a bottom surface 808. The recess 804 may extend through less than an entire thickness of the cap 800 so that when the cap 800 is coupled with a water bottle 714 sterility can be maintained. The portion 810 of the cap 800 adjacent to the indent 804 may be sufficiently thin as to allow the tubular port 708 to puncture through the portion 810 of the cap 800 adjacent to the indent 804 to fluidly couple the water bottle 714 with the container 702.

FIG. 8B depicts a perspective view of another illustrative puncturable cap 850. The cap 850 may be configured to be secured to a mouth of the water bottle 714. For example, the cap 850 may include an annular side wall 852 configured to surround the mouth of the water bottle 714. The cap 850 may be configured to form a snap fit or threadably engage the water bottle 714. Other mechanical engagements may be used, as desired. The cap 850 may further include perforations 854 formed in a top surface 856 of the cap 850. In the illustrated embodiment, the perforations form an "X" shape, however, other shapes and configurations may be used as desired. The perforations 854 may extend through less than an entire thickness of the cap 850 so that when the cap 850 is coupled with a water bottle 714 sterility can be maintained while creating an area of weakness to allow the tubular port 708 to puncture through the perforations 854 of the cap 850 adjacent to the indent 804 to fluidly couple the water bottle 714 with the container 702.

Figure 9:
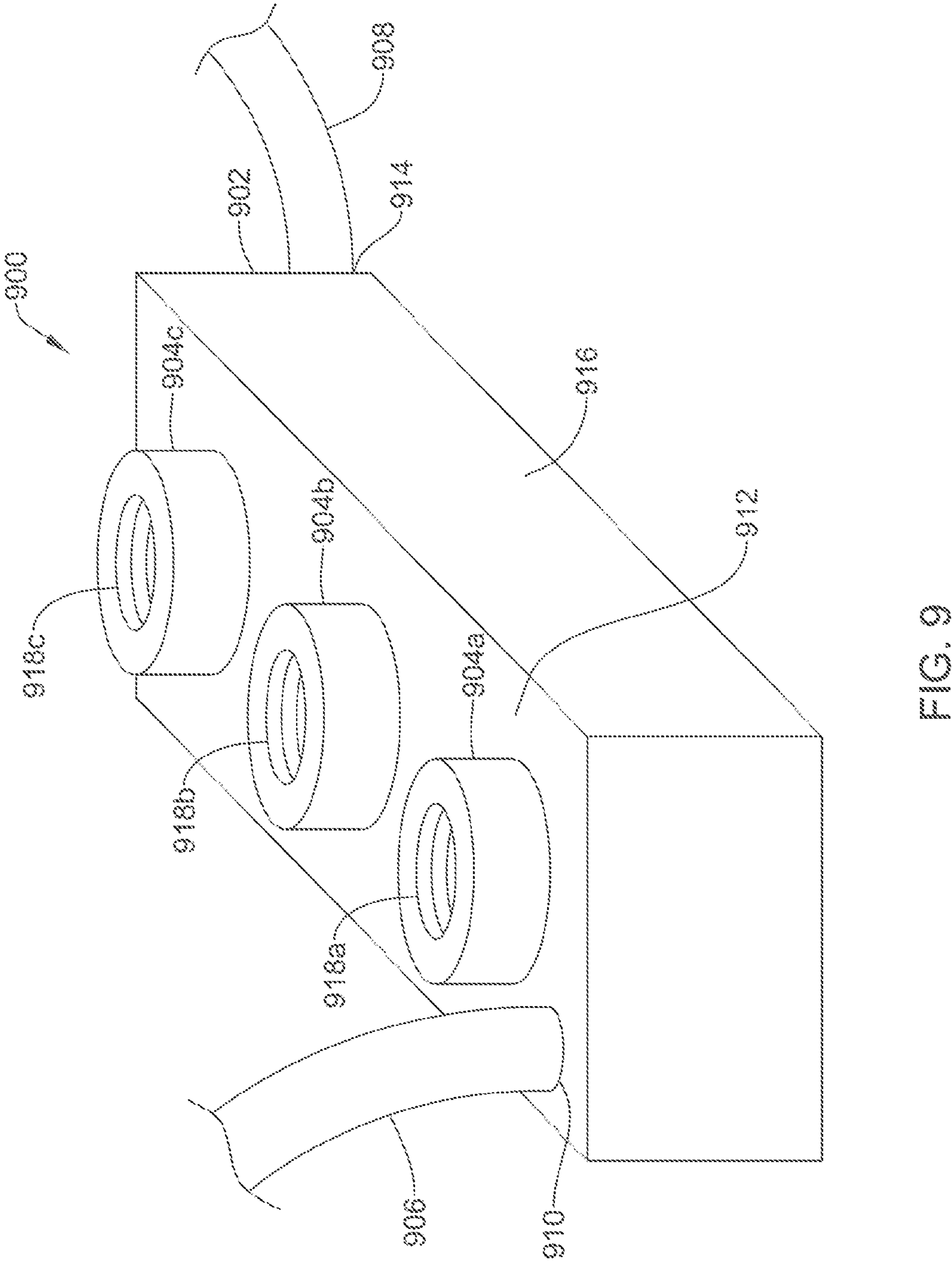
FIG. 9 depicts a perspective view of another illustrative refillable fluid reservoir.

FIG. 9 depicts a perspective view of another illustrative refillable fluid reservoir 900. The reservoir 900 may be configured to be used in an endoscopic system and includes components similar to the endoscope and endoscope systems described with regard to FIGS. 1-4; however, not all features may be described or shown here if not pertinent to the fluid circuit of the system. The reservoir 900 includes a container 902 defining a cavity configured to hold a fluid. The container 902 may be formed from a lightweight, flexible material, such as, but not limited to low density polyethylene (LDPE), thermoplastic polyurethane (TPU), silicone, polyethylene terephthalate (PET), aluminum, nylon, polyethylene (PE), or combinations thereof, etc. In other embodiments, the container 902 may be formed from a semi-rigid or rigid material, such as, but not limited to polyethylene terephthalate (PET), polypropylene (PP), etc. In some embodiments, the container 902 may be entirely translucent, entirely opaque, or combinations thereof.

The container 902 may be sized and shaped to hold of volume of fluid. In some cases, the volume of fluid may be approximately equal to 1 liter (e.g., the typical volume of a water bottle provided in medical procedures). In other embodiments, the container 902 may have a volume greater than 1 liter. In yet other embodiments, the container 902 may have a volume of less than one liter. It is contemplated that when the volume of the container 902 is less than 1 liter, container 902 may be coupled to a fluid source, such as, but not limited to, one or more water bottles (not explicitly shown) during a procedure. While the container 902 is illustrated as having a generally rectangular prism shape, the container 902 may take other forms, as desired. It is further contemplated that the reservoir 900 may be provided as a manifold configured to interface with another reservoir to provide a means for refilling the additional reservoir.

The reservoir 900 may further include a plurality of ports 904*a*, 904*b*, 904*c* each having a removable cap or plug (not explicitly shown). While the reservoir 900 is illustrated as including three ports 904*a-c*, the reservoir 900 may include fewer than three or more than three ports 904*a-c*, as desired. The caps may be configured to form a fluid tight seal with the ports 904*a-c*. The caps may be configured to threadably engage the ports 904*a-c*, form a friction fit with the ports 904*a-c*, form a snap fit with the ports 904*a-c*, or otherwise releasably engage the ports 904*a-c*. In some embodiments, the cap may be a self-sealing one-way valve. In other embodiments, the caps may be formed from a self-healing material. For example, a needle may be used to puncture a self-healing material and once the needle is removed, the hole formed by the needle is sealed without user intervention. Portions of the ports 904*a-c* may extend into the container 902. The removable caps may be removed to place a fluid source in selective fluid communication with the container 902 and allow fluid to be poured through a lumen of the ports 904*a-c* and into the container 902.

The reservoir 900 may be connected in fluid communication with a tubing manifold (not explicitly shown) via a shared gas supply/alternate gas supply tubing (or gas supply tubing) 906 and a lens wash supply/irrigation supply tubing 908. The shared gas supply tubing 906 extends from a second end external to the reservoir 900 through a reservoir opening 910 in the top portion 912 of the container 902. The shared gas supply tubing 906 may terminate within a reservoir gap, at or below the opening 910, but not extending into the remaining fluid in the container 902. However, in some cases, the gas supply tubing 906 may extend into the fluid. For example, the opening 910 may be at a bottom or side of the container 902 such that the shared gas supply tubing 906 terminates within the fluid with gas bubbling up through the fluid to pressurize the container 902. A lumen extends through the gas supply tubing 906 for receiving a flow of air and/or gas therethrough. The lumen of the gas supply tubing 906 is in operative fluid communication with the top portion 912 of the reservoir 900.

The water supply tubing 908 extends from a second end external to the reservoir 900 through a reservoir opening 914, terminating in a first end within the remaining fluid at or substantially at the bottom portion 916 of the container 902. A lumen extends through the water supply tubing 908 for receiving a flow of fluid therethrough. The lumen of the lens wash supply/irrigation supply tubing 908 is in selective operative fluid communication with the bottom portion of the container 902. In the illustrated embodiment, the gas supply tubing 906 and the water supply tubing 908 may enter/exit the container 902 through separate openings 910, 914. However, this is not required. For example, the gas supply tubing 906 and the water supply tubing 908 may be coaxially arranged and enter the container 902 through a common opening. The openings may include a grommet or heat seal configured to seal the container 902 about the tubing 906, 908 in a fluid and pressure tight manner. In other embodiments, a manifold may be used to couple the tubing 906, 908 to the reservoir 900 in a fluid-tight manner.

A portion of a gas supply tubing 906 and a portion of lens wash supply tubing 908 may be connected in fluid communication with the endoscope at gas/lens wash connection on the connector portion 265 of the umbilical. The gas supply tubing 906 is connected in fluid communication with a gas pump (not explicitly shown) and gas feed line (not explicitly shown), and the lens wash supply tubing 908 is connected in fluid communication with lens wash feed line (not explicitly shown), within connector portion 265. In some examples, the gas supply tubing 906 may include a manifold to fluidly couple portions of the gas supply tubing 906. Similarly, the lens wash supply tubing 908 may include a manifold to fluidly couple portions of the lens wash supply tubing with the shared lens wash/irrigation (or water) supply tubing 908. While not explicitly shown, irrigation supply tubing may be coupled to the manifold, if so provided, to supply irrigation fluid from the reservoir 900. In other cases, a separate irrigation supply tube may be provided.

It is contemplated that the reservoir 900 may be filled and refilled as needed by removing the cap and coupling the water source to the ports 904*a-c*. It is contemplated that the reservoir 900 may be inverted (relative to illustrated orientation) to allow the water bottles to be secured to the reservoir 900 with the water bottles in an upright orientation (to limit spillage). In some embodiments, the ports 904*a-c* may include internal threads 918*a*, 918*b*, 918*c*, or other coupling feature, configured to engage mating external threads, or other coupling feature on the water source. Once the water bottles are coupled to the reservoir 900, the reservoir 900 can be returned to its original configuration (e.g., with ports 904*a-c* facing up) to allow gravity to draw water from the water bottles into the cavity of the reservoir 900. The refilling of the reservoir 900 may be performed during a procedure or between procedures, as necessary. The water may be sterile or non-sterile, as desired. For example, sterile water may be used for therapeutic procedures while non-sterile water may be used for diagnostic procedures. It is contemplated that refilling the reservoir 900 with sterile or non-sterile water may create more flexibility and reduce the need to have as much sterile water in storage. Further, refilling the reservoir 900 via the ports 904*a-c* and removable cap may also remove the need to disconnect the reservoir 900 from the tubing 906, 908 throughout the day eliminating or greatly reducing the possibility of cross contamination by removing the need to replace the water container.

In some embodiments, the water bottles may remain coupled to the reservoir 900 during use of the endoscope. For example, the container 902 does not necessarily need to store water for use during the procedure. Instead, the container 902 may function to transfer water from the water bottles to the endoscope. It is further contemplated that not all of the ports 904*a-c* have a water bottle coupled thereto.

For example, two ports 904*a*, 904*b* may be coupled to water bottles while the third port 904*c* is capped off. This is just one example, other port combinations or only a single port may be utilized, as desired.

Figure 10:
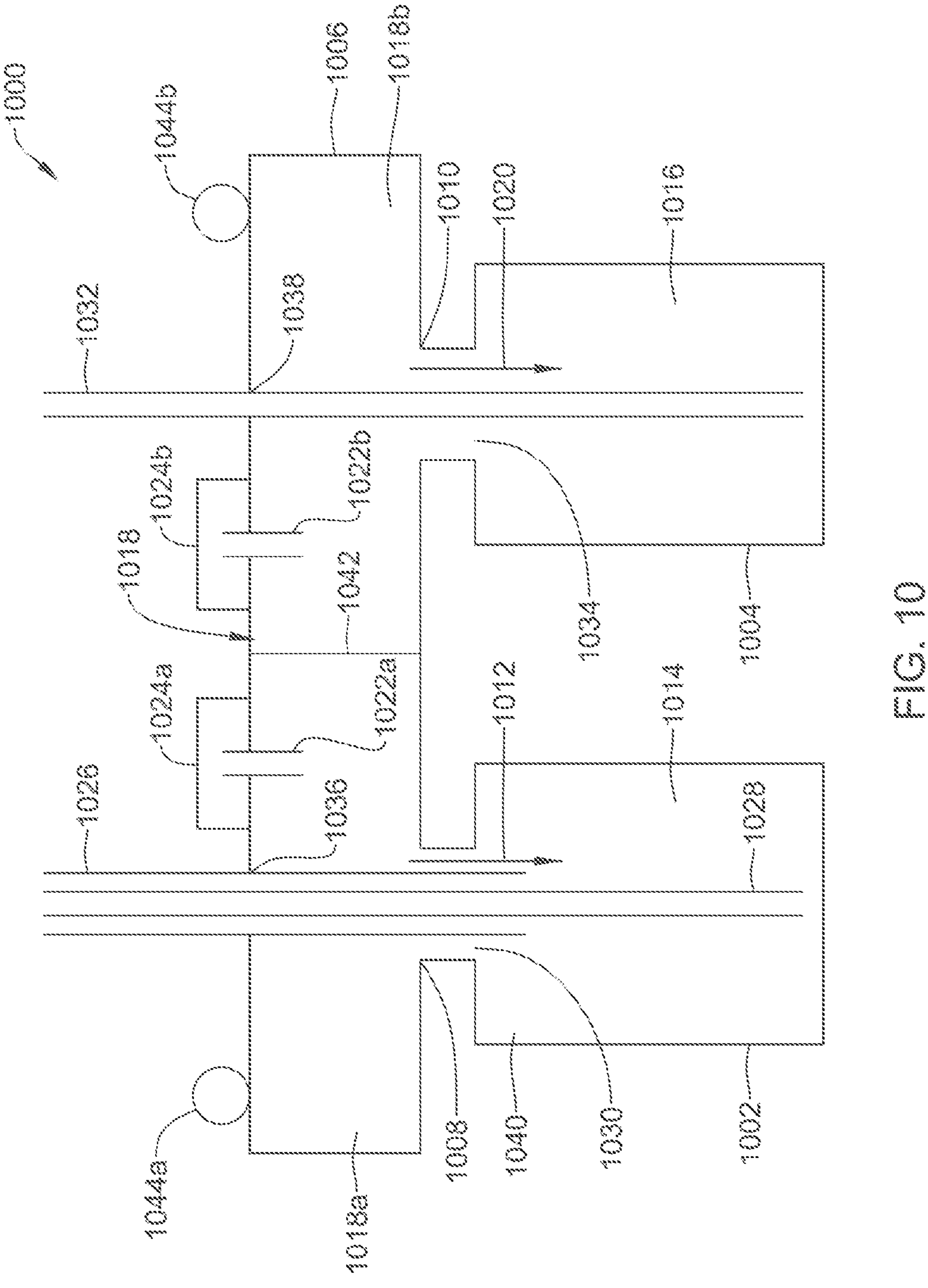
FIG. 10 depicts a perspective view of another illustrative refillable fluid reservoir system.

FIG. 10 depicts a perspective view of another illustrative refillable fluid reservoir system 1000. The reservoir system 1000 may be configured to be used in an endoscopic system and includes components similar to the endoscope and endoscope systems described with regard to FIGS. 1-4; however, not all features may be described or shown here if not pertinent to the fluid circuit of the system. The reservoir system 1000 includes a first container 1002 defining a cavity configured to hold a fluid and a second container 1004 defining a cavity configured to hold a fluid. In some embodiments, the first container 1002 may be used for insufflation and lens wash while the second container 1004 may be used for irrigation.

The first container and/or second containers 1002, 1004 may be formed from a lightweight, flexible material, such as, but not limited to low density polyethylene (LDPE), thermoplastic polyurethane (TPU), silicone, polyethylene terephthalate (PET), aluminum, nylon, polyethylene (PE), or combinations thereof, etc. In other embodiments, the first and/or second containers 1002, 1004 may be formed from a semi-rigid or rigid material, such as, but not limited to polyethylene terephthalate (PET), polypropylene (PP), etc. In some embodiments, the first and/or second containers 1002, 1004 may be entirely translucent, entirely opaque, or combinations thereof.

The first and second containers 1002, 1004 may be sized and shaped to hold of volume of fluid. In some cases, the volume of fluid may be approximately equal to 1 liter (e.g., the typical volume of a water bottle provided in medical procedures). In other embodiments, the first and/or second containers 1002, 1004 may have a volume greater than 1 liter. In yet other embodiments, the first and/or second containers 1002, 1004 may have a volume of less than one liter. While the first and/or second containers 1002, 1004 may take any shape desired, such as, but not limited, cylindrical, rectangular prism, a flexible bag, etc.

The first and/or second containers 1002, 1004 may each be fluidly coupled to a water storage chamber 1006. The water storage chamber 1006 may be configured to store excess water which may be used to refill or supply the first and/or second containers 1002, 1004 with water as water is depleted from the first and/or second containers during an endoscopic procedure. It is contemplated that water may flow into the first and/or second containers 1002, 1004 from the water storage chamber 1006 (as long as water is present in the water storage chamber 1006) without user intervention water is removed from the respective container 1002, 1004. The water storage chamber 1006 may include an optional partition 1042 positioned within a chamber 1018 of the water storage chamber 1006 and configured to divide the water storage chamber 1006 into a first sub-chamber 1018*a* and a second sub-chamber 1018*b*. The first sub-chamber 1018*a* and the second sub-chamber 1018*b* may be fluidly isolated from one another.

The first container 1002 may be coupled to the water storage chamber 1006 at a first connection point 1008 defining a through hole and the second container 1004 may be coupled to the water storage chamber 1006 at a second connection point 1010 defining a through hole. In some embodiments, the first and/or second containers 1002, 1004 may threadably engage the water storage chamber 1006 at the connection points 1008, 1010. In other embodiments, the first and/or second containers 1002, 1004 may form a snap fit or friction fit with the water storage chamber 1006. The securement method for coupling the first and/or second containers 1002, 1004 to the water storage chamber 1006 may be selected to form a fluid tight seal between the first and second containers 1002, 1004 and the water storage chamber 1006. While not explicitly shown, gaskets, O-rings, or other sealing members may be positioned between the first and second containers 1002, 1004 and the water storage chamber 1006 to help form a fluid tight seal. Fluid may flow from the first sub-chamber 1018*a* of the water storage chamber 1006 to an interior 1014 of the first container 1002 along a first fluid path 1012. Similarly, fluid may flow from the second sub-chamber 1018*b* of the water storage chamber 1006 to an interior 1016 of the second container 1004 along a second fluid path 1020. When the partition 1042 is not included, fluid may flow from a common chamber into either the first container 1002 or the second container.

The water storage chamber 1006 may include a first port 1022*a* for receiving a flow of water into the first sub-chamber 1018*a* of the water storage chamber 1006 and a second port 1022*b* for receiving a flow of water into the second sub-chamber 1018*b* of the water storage chamber 1006. The ports 1022*a-b* may each include a removable seal 1024*a*, 1024*b*, such as, but not limited to, a cap, plug, lid, etc. As the first fluid path 1012 allows air/gas from the first container 1002 to enter at least part of the water storage chamber 1006, the seals 1024*a-b* may be removably coupled to the ports 1022*a-b* in a manner that allows the seals 1024*a-b* to remain coupled with the ports 1022*a-b* when the first container 1002 is pressurized for lens cleaning. In some embodiments, such as when the partition 1042 is not included, the water storage chamber 1006 may include only a single port and seal.

The first container 1002 may be connected in fluid communication with a lumen of a gas supply tube 1026 and a lumen of a water supply tube 1028. The gas supply tube 1026 and the water supply tube 1028 may be provided in a shared length of tubing. The gas supply tube 1026 and the water supply tube 1028 may be coaxially arranged with the water supply tube 1028 extending within and through the lumen of the gas supply tube 1026 along a portion of the length of the gas supply tube 1026. However, this is not required. In some cases, the gas supply tube 1026 and the water supply tube 1028 may extend side by side. The gas supply tubing 1026 extends from a second end to a first end adjacent to an opening 1030 in the first container 1002. In the use configuration, the second end of the gas supply tubing 1026 may be external to the first container 1002. A lumen extends through the gas supply tube 1026 for receiving a flow of air and/or gas therethrough. The lumen of the gas supply tube 1026 is in fluid communication with the first container 1002. The first end of the gas supply tubing 1026 is in selective fluid communication with the top portion 1030 of the first container 1002 in the embodiment shown. In other embodiments, the gas supply tubing 1026 may be connected at other regions of the first container 1002, such as, but not limited to, a bottom portion or a side portion. The water supply tubing 1028 extends from a second end to a first end which extends through the opening 1030 and into an interior of the first container 1002. In the use configuration, the second end of the water supply tubing 1028 may be external to the first container 1002. A lumen extends through the water supply tube 1028 for receiving a flow of fluid therethrough. The second ends of the gas supply tube 1026 and the water supply tube 1028 may be coupled to a manifold (if so provided) or a connector portion 265 of an endoscope system. The first end of the water supply tube 1028 is in selective fluid communication with the bottom portion of the first container 1002.

In some embodiments, the second container 1004 may be connected in fluid communication with a lumen of an irrigation supply tube 1032. The irrigation supply tubing 1032 extends from a second end to a first end which extends through an opening 1034 and into an interior 1016 of the second container 1004. In the use configuration, the second end of the irrigation supply tubing 1032 may be external to the second container 1004. A lumen extends through the irrigation supply tube 1032 for receiving a flow of fluid therethrough. In some cases, the irrigation supply tube 1032 may be coupled to a manifold, if so provided. The first end of the irrigation supply tube 1032 is in selective fluid communication with the bottom portion of the second container 1004.

The second ends of the gas supply tubing 1026 and the lens wash supply tubing 1028 may be connected in fluid communication with the endoscope at gas/lens wash connection on the connector portion 265 of the umbilical. The gas supply tubing 1026 is connected in fluid communication with a gas pump (not explicitly shown) and gas feed line (not explicitly shown), and the lens wash supply tubing 1028 is connected in fluid communication with lens wash feed line (not explicitly shown), within connector portion 265. The irrigation tubing 1032 is connected in fluid communication with the irrigation supply line 255*c* via an irrigation pump 315.

The gas supply tubing 1026, lens wash supply tubing 1028, and irrigation tubing 1032 may be pre-installed with the water storage chamber 1006. For example, the gas supply tubing 1026 and lens wash supply tubing 1028 may be slidably disposed within a first opening 1036 formed in the water storage chamber 1006. The first opening 1036 may be generally aligned with the first connection point 1008. Once the first container 1002 is coupled to the water storage chamber 1006, the gas supply tubing 1026 and lens wash supply tubing 1028 may be pushed down into the interior 1014 of the first container 1002. The first opening 1036 may include a seal or gasket to provide a pressure tight seal around the gas supply tubing 1026. Similarly, the irrigation tubing 1032 may be slidably disposed within a second opening 1038 formed in the water storage chamber 1006. The second opening 1038 may be generally aligned with the second connection point 1010. Once the second container 1004 is coupled to the water storage chamber 1006, the irrigation tubing 1032 may be pushed down into the interior 1016 of the second container 1004. The second opening 1038 may include a seal or gasket to provide a pressure tight seal around the irrigation tubing 1032. However, in other embodiments, the gas supply tubing 1026, lens wash supply tubing 1028, and/or irrigation tubing 1032 may by-pass the water storage chamber 1006 and be coupled to the first container 1002 and/or second container 1004 at alternative locations.

The water storage chamber 1006 may further include one or more supports 1044*a*, 1044*b* affixed thereto. The supports 1044*a-b* may be configured to engage one or more hooks to allow the reservoir system 1000 to be hung or elevated off the ground. For example, the supports 1044*a-b* may engage hooks on an IV stand. The supports 1044*a-b* may be rings, hooks, clasps, etc. While the supports 1044*a-b* are illustrated as being positioned adjacent to an upper end of the water storage chamber 1006, it is contemplated that the supports 1044*a-b* may be positioned at other locations, such as, but not limited to, a back side of the water storage chamber 1006. Further, while the illustrated embodiment includes two supports 1044*a-b*, fewer than two or more than two supports may be provided, as desired.

It is contemplated that the reservoir system 1000 may be filled and refilled as needed. The first and second sub-chambers 1018*a-b* may be filled individually as needed or substantially simultaneously by removing one or both of the seals 1024*a-b* and coupling the water source to one or both of the ports 1022*a-b*. In some embodiments, the ports 1022*a-b* may include internal threads, or other coupling feature, configured to engage mating external threads, or other coupling feature on the water source. In other embodiments, the ports 1022*a-b* may be a basin configured to receive a flow of water from the water source. For example, water may be poured from the water source into the ports 1022*a-b*. In some cases, the more than one water bottle may be used to fill the first and/or second sub-chambers 1018*a-b*.

Figure 11:
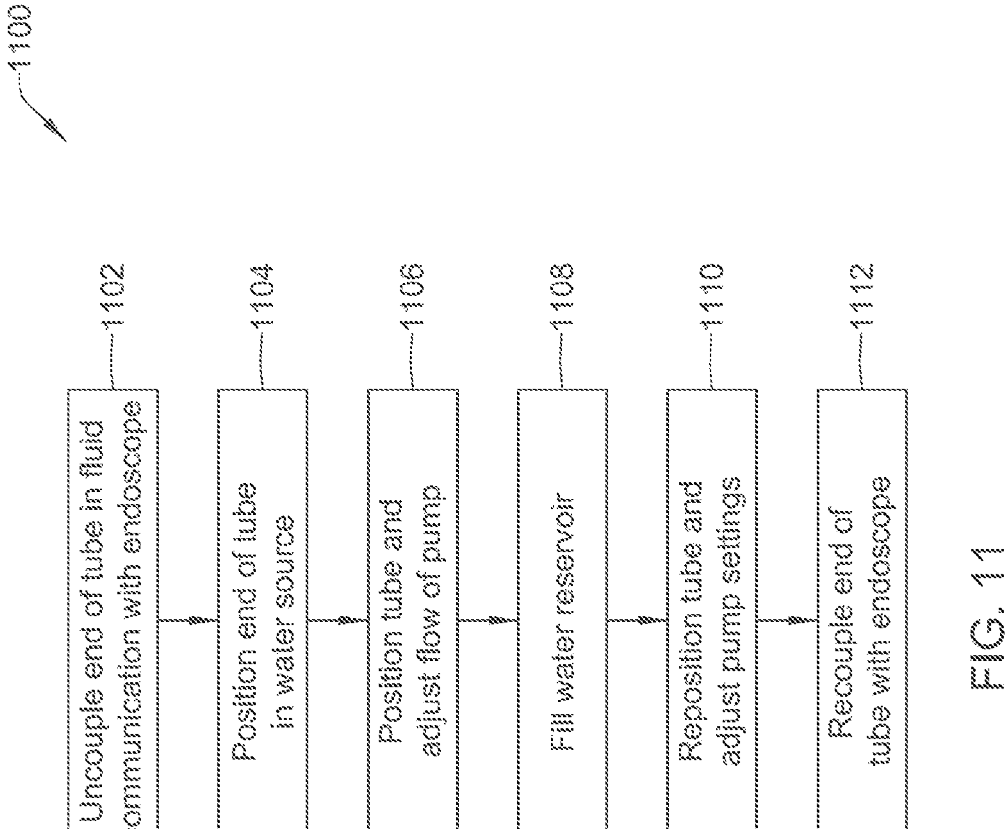
FIG. 11 is a flow chart of an illustrative method for filling a refillable water reservoir.

FIG. 11 is a flow chart of an illustrative method 1100 for filling a refillable water reservoir. The method may be configured to be used in an endoscopic system and includes components similar to the endoscope and endoscope systems described with regard to FIGS. 1-4; however, not all features may be described or shown here if not pertinent to the fluid circuit of the system. It is contemplated that the existing components in an endoscope system 200 may be used to refill water reservoir, such as water reservoirs 270, 305, 405. When the endoscope 100 is not in use, the user may uncouple an end of a water supply tubing from a connector portion 265 in fluid communication with the endoscope 100, as shown at block 1102. The water supply tubing may be either the lens wash tubing 245*c* or the irrigation supply tubing 325*c*. The uncoupled end of the water supply tubing may then be positioned within a water source (e.g., a water bottle) in fluid communication with the water therein, as shown at block 1104. Adjustments may then be made the water supply tube and/or a flow of a pump as shown at block 1106. The adjustments may vary depending on whether the lens wash tubing 245*c* or the irrigation supply tubing 325*c* is used.

When the lens wash tubing 245*c* is used, an intermediate portion of the lens wash tubing 245*c* may be positioned within a pump. In some cases, the pump may be the irrigation pump 315. In other embodiments, a separate pump, such as a peristaltic pump, may be provided to pump water from the water source to the water reservoir 270, 305, 405. Once the lens wash tubing 245*c* is positioned within the pump, a direction of flow and/or a speed of the pump may then be adjusted. For example, the direction of flow through the lens wash tubing 245*c* during refilling of the water reservoir 270, 305, 405 is opposite the direction of flow during use of the endoscope 100.

The irrigation supply tubing 325*c* may include an outflow check valve or a one-way valve to prevent water from flowing back to the water reservoir. If such a valve is provided, the endoscope system 200 may include a by-pass which allows for reverse flow of water through the irrigation supply tubing 325*c* as the direction of flow through the irrigation supply tubing 325*c* during refilling of the water reservoir 305, 405 is opposite the direction of flow during use of the endoscope 100. As the irrigation supply tubing 325*c* is already assembled with the irrigation pump 315, no adjustments to the intermediate portion of the irrigation supply tubing 325*c* may be required. The direction of the pump 315 may reversed to reverse the flow of fluid through the irrigation supply tubing 325*c* and a speed of the pump 315 may be adjusted.

Once the water supply tubing is positioned and the pump adjusted, the water reservoir 270, 305, 405 may be filled, as shown at block 1108. This may include starting or activating the pump to pump water from the water bottle through the water supply tubing to the reservoir. The pump may be deactivated when the water reservoir 270, 305, 405 is full or when the water source is empty. In some cases, more than one water bottle may be required to fill the water reservoir 270, 305, 405. In such an instance, the pump may be stopped when the current water source is empty, the end of the of the water supply tubing transferred to a new or fresh water source, and the pump restarted. This may be repeated with as many water sources or water bottles necessary to fill the water reservoir 270, 305, 405.

Once the water reservoir 270, 305, 405 is full, the water supply tubing may be returned to its original configuration, as shown at block 1110. If the lens wash tubing 245*c* is used, the lens wash tubing 245*c* may be removed from the pump. If the irrigation supply tubing 325*c* is used, the one-way valve by-pass is reversed to once again prevent water from flowing back to the water reservoir. The irrigation pump 315 may be returned to its original direction of flow and the speed adjusted to provide the desired flow rate for an endoscopic procedure. Finally, the end of the water supply tubing may be removed from the water source and coupled with the connector portion 265, as shown at block 1112.

As will be appreciated, the lengths of irrigation, lens wash, gas supply, alternate gas supply tubing may have any suitable size (e.g., diameter). In addition, the sizing (e.g., diameters) of the tubing may vary depending on the application. In one non-limiting embodiment, the irrigation supply tubing may have an inner diameter of approximately 6.5 mm and an outer diameter of 9.7 mm. The lens wash supply tubing may have an inner diameter of approximately 5 mm and an outer diameter of 8 mm. The gas supply tubing may have an inner diameter of approximately 2 mm and an outer diameter of 3.5 mm. The alternative gas supply tubing may have an inner diameter of approximately 5 mm and an outer diameter of 8 mm.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases “at least one”, “one or more”, and “and/or”, as used herein, are open-ended expressions that are both conjunctive and disjunctive in operation. The term “a” or “an” entity, as used herein, refers to one or more of that entity. As such, the terms “a” (or “an”), “one or more” and “at least one” can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader’s understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term “comprises/comprising” does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms “a”, “an”, “first”, “second”, etc., do not preclude a plurality. Reference signs in the claims are provided merely as a clarifying example and shall not be construed as limiting the scope of the claims in any way.

What is claimed is:

1. A reservoir arranged and configured to couple to an endoscope for use in an endoscopic procedure, the reservoir comprising:

a first container configured to contain a fluid therein, the first container having a first water outlet and a gas inlet;

a second container configured to contain a fluid therein, the second container having a second water outlet;

a chamber in fluid communication with the first container and the second container, the chamber including one or more ports, wherein the one or more ports is configured to selectively fluidly couple the chamber with an external water source;

a water supply tube including a first end, a second end, and a first lumen extending therethrough, wherein the first lumen is in fluid communication with the first container and the second end of the water supply tube is positioned external to the chamber and the first container; and a gas supply tube including a first end, a second end, and a second lumen extending therethrough, wherein the second lumen is in operative fluid communication with the first container and the second end of the gas supply tube is positioned external to the chamber and the first container, wherein the first lumen and the second lumen each extend through the chamber.

2. The reservoir of claim 1, wherein the first and second containers are threadably engaged with the chamber.

3. The reservoir of claim 1, further comprising:

an irrigation supply tube including a first end, a second end, and an irrigation lumen extending therethrough, wherein the irrigation lumen is in fluid communication with the second container and the second end of the irrigation supply tube is positioned external to the chamber and the second container.

4. The reservoir of claim 3, wherein the irrigation lumen extends through the chamber.

5. The reservoir of claim 1, further comprising one or more supports coupled to the chamber, the one or more supports configured to engage one or more hooks.

6. The reservoir of claim 1, further comprising a partition positioned within the chamber partitioning the chamber into a first sub-chamber and a second sub-chamber.

7. The reservoir of claim 6, wherein the one or more ports comprises a first port in fluid communication with the first sub-chamber and a second port in fluid communication with the second sub-chamber.

8. The reservoir of claim 6, wherein the first sub-chamber is in fluid communication with the first container and the second sub-chamber is in fluid communication with the second container.

* * * * *